United States Patent [19]

Meanwell et al.

[11] Patent Number: 4,775,674

[45] Date of Patent: Oct. 4, 1988

[54] IMIDAZOQUINOLINYLETHER DERIVATIVES USEFUL AS PHOSPHODIESTERASE AND BLOOD AGGREGATION INHIBITORS

[75] Inventors: Nicholas A. Meanwell, Mt. Vernon; John J. Wright, Evansville, both of Ind.

[73] Assignee: Bristol-Myers Company, New York, N.Y.

[21] Appl. No.: 866,813

[22] Filed: May 23, 1986

[51] Int. Cl.⁴ .................. C07D 471/04; C07D 413/14; C07D 401/14; A61K 31/47
[52] U.S. Cl. ...................... 514/293; 546/82; 544/126; 544/361; 514/253; 514/232.8
[58] Field of Search .................. 546/82; 544/126, 361; 514/227, 255, 293

[56] References Cited

U.S. PATENT DOCUMENTS

| 3,932,407 | 1/1976 | Beverung, Jr. et al. | 544/250 |
| 4,256,748 | 3/1981 | Chodnekar et al. | 514/267 |
| 4,490,371 | 12/1984 | Jones et al. | 514/234 |

FOREIGN PATENT DOCUMENTS

153152 8/1985 European Pat. Off. .............. 546/81

OTHER PUBLICATIONS

Kozak, et al., *Bull. Intern. Acad. Polonaise*, 1930A, 432–438 (Chem. Abs., 25, 5400).

Musial, *Roczniki Chem.*, 1951, 25, 46–52 (Chem. Abs., 1953, 47, 4885f).
Fryer, et al., *J. Org. Chem.*, 1977, 42, 2212–2219.
Reid, et al., *Chem. Ber.*, 1956, 89 2684–2687.
Fleming et al., *New Drugs Annual: Cardiovascular Drugs*, Raven Press, pp. 277–294, New York (1983).

*Primary Examiner*—Mary C. Lee
*Assistant Examiner*—Zinna Northington
*Attorney, Agent, or Firm*—Robert H. Uloth

[57] ABSTRACT

Novel series of 2,3-dihydro-2-oxo-1H-imidazo[4,5-b]quinolinyl ether derivatives of formula

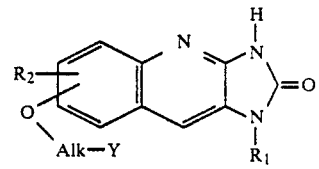

wherein $R_1$ is hydrogen, lower alkly, benzyl; $R_2$ is hydrogen, halogen, lower alkyl, lower alkoxy; Alk is alkylene; Y is hydroxy and alkanoic or aralkanoic esters thereof, oxo ketone, dialkylamino, carboxylic acid and esters, carboxamides, alkoxy, ethanolamines and cyclic carbamates thereof, tetrazolyl, and optionally substituted phenylsulfonyl. The compounds are cyclic AMP phosphodiesterase inhibitors and are particularly useful as inhibitors of blood platelet aggregation and/or as cardiotonic agents.

56 Claims, No Drawings

IMIDAZOQUINOLINYLETHER DERIVATIVES USEFUL AS PHOSPHODIESTERASE AND BLOOD AGGREGATION INHIBITORS

BACKGROUND OF THE INVENTION

This invention generally pertains to heterocyclic carbon compounds having drug and bio-affecting properties and to their preparation and use. In particular, the invention is concerned with a series of new 2,3-dihydro-2-oxo-1H-imidazo[4,5-b]quinolinylether derivatives which are phosphodiesterase inhibitors, blood platelet antiaggregators and cardiotonic agents. According to conventional nomenclature, the basic heterocyclic structure can be referred to as 1,3-dihydro-2H-imidazo[4,5-b]quinolin-2-one.

As a structural class, relatively few 1,3-dihydro-2H-imidazo[4,5-b]quinolin-2-ones are known to applicants with the following chemical literature illustrative of the art.

Kozak, et al., *Bull. Intern. Acad. Polanaise*, 1930A, 432–438 (Chem. Abs. 25, 5400) describes the unsubstituted compound 1,3-dihydro-2H-imidazo[4,5-b]quinolin-2-one of formula (1).

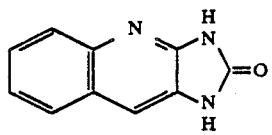

Musial, *Roczniki Chem.*, 1951, 25, 46–52 (Chem. Abs., 1953, 47, 4885f) synthesized 1,3-derivatives of (1) as illustrated in formula (2).

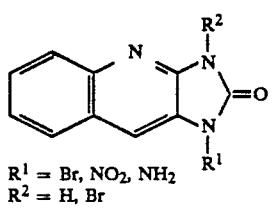

$R^1$ = Br, NO$_2$, NH$_2$
$R^2$ = H, Br

Fryer, et al., *J. Org. Chem.*, 1977, 42, 2212–2219 describes the 3,7,9-trisubstituted compound of formula (3).

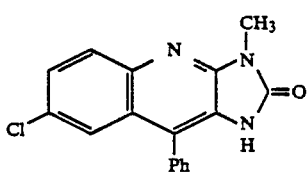

Reid, et al., *Chem. Ber.*, 1956, 89, 2684–2687 describes the synthesis of the 1,3-diphenyl derivative of formula (4).

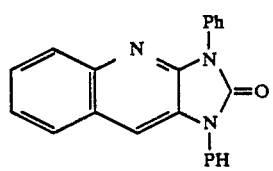

No pharmacological utility is taught for the 1,3-dihydro-2H-imidazo[4,5-b]quinolin-2-one structures disclosed in the aforementioned references which are of a chemical nature.

Various derivatives of the tetrahydroimidazo[2,1-b]quinazolin-2-one (5) heterocycle have been studied for their platelet inhibition and cardiotonic properties.

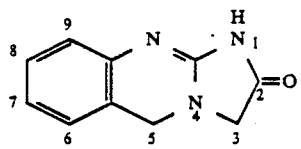

For example:

Beverung, Jr., et al., U.S. Pat. No. 3,932,407 disclose a series of compounds useful as blood platelet antiaggregative and/or antihypertensive and/or bronchodilator agents of the tetrahydroimidazo[2,1-b]quinazolin-2-one class. Anagrelide (6), a particularly preferred member of the Beverung, Jr., et al. series, has been studied extensively, e.g., J. S. Fleming, et al., *New Drugs Annual: Cardiovascular Drugs*, Raven Press, pages 277–294, New York (1983).

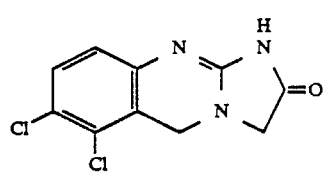

Chodnekar, et al., U.S. Pat. No. 4,256,748 describes a series of tetrahydroimidazo[2,1-b]quinazolin-2-ones of the formula (7) as inhibitors of the aggregation of blood platelets and cardiotonic activity.

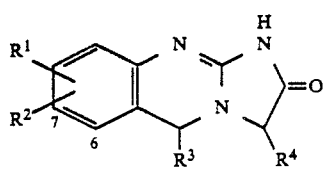

Representative of the Chodneker compounds are RO 15-2041 ($R^4$=CH$_3$, $R^3$=H, $R^2$=6—CH$_3$, $R^1$=7—Br) and RO 13-6438 ($R^4$=CH$_3$, $R^3$=H, $R^2$=6—CH$_3$, $R^1$=H).

Jones, et al., U.S. Pat. No. 4,490,371 describes another series of tetrahydroimidazo[2,1-b]quinazolin-2-one derivatives as cyclic AMP phosphodiesterase inhibitors useful as thrombogenic agents. Among the compounds disclosed is the formula (8) amide, identified in the art as RS82856.

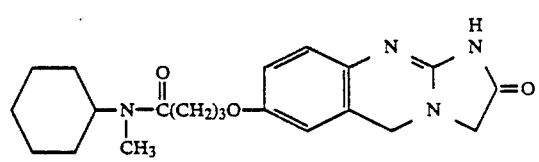

Jones, et al., European Patent Application No. 153152 further describes tetrahydroimidazo[2,1-b]quinazolin-2-ones of formula (9) as cyclic AMP phosphodiesterase inhibitors useful as antithrombogenic agents.

$$\text{(9)}$$

[Structure 9: R₅—NCO(CH₂)ₙO— substituted phenyl with (CH₂)ₙCOZ and imidazolinone ring system; Y substituent; R₁, R₂, R₃, R₄ groups]

SUMMARY OF THE INVENTION

In its broadest aspect, this invention is concerned with a new series of 2,3-dihydro-2-oxo-imidazo[4,5-b]quinolinyl derivatives having valuable pharmacological properties which makes them particularly useful as cardiotonic agents and/or inhibitors of phosphodiesterase and mammalian blood platelet aggregation. Formula I illustrates the compounds of the invention and the ring numbering system used herein.

[Structure: Imidazo[4,5-b]quinoline ring system with numbering 1-9, substituents R₂ at position 6, O at position 7 with Alk—Y, R₁ on N1, H on N3, =O on C2, N4]

In the foregoing formula:

R₁ is hydrogen, lower alkyl, benzyl;
R₂ is hydrogen, halogen, lower alkyl, lower alkoxy;
Alk is an unbranched or branched alkylene chain of 1 to 8 carbon;
Y is hydroxyl and esters thereof formed with an alkanoic acid of 1 to 6 carbon atoms or arylalkanoic acid of 7–12 carbon atoms, alkoxy wherein with Alk the number of carbon atoms ranges from 2 to 10, oxo forming a ketone, di-(lower alkyl)amino, —CO₂H, —CO₂R₃ wherein R₃ is lower alkyl;

$$-\overset{\overset{\displaystyle O}{\|}}{C}N\overset{R_4}{\underset{R_5}{<}}$$

wherein R₄ is hydrogen, lower alkyl, benzyl, cyclohexyl, —(CH₂)ₙCO₂R₆ wherein n is the integer 1 to 8 and the alkylene chain (CH₂)ₙ is unbranched or branched and R₆ is hydrogen or lower alkyl;
R₅ is hydrogen, lower alkyl, benzyl, adamantanamyl, cycloalkyl of 3 to 7 carbon atoms wherein the cycloalkyl ring is unsubstituted or substituted with lower alkyl or lower alkoxy;
R₄ and R₅ are joined together to form morpholinyl, piperidinyl optionally substituted with —CO₂R₇ wherein R₇ is hydrogen or lower alkyl,
4-phenylpiperazinyl wherein phenyl is unsubstituted or independently substituted with up to 2 halogen, lower alkyl, or lower alkoxy groups;

[Structure: N-R₈ substituted ring with O and =O]

wherein R₈ is lower alkyl;

$$-\overset{\overset{\displaystyle OH}{|}}{C}HCH_2NH-R_8$$

wherein R₈ is lower alkyl;

[Structure: tetrazole ring with N—N, N—N, and R₉ substituent]

wherein R₉ is lower alkyl, cycloalkyl of 5 to 7 carbon atoms;
—SO₂—phenyl wherein phenyl is unsubstituted or independently substituted with up to 2 halogen, lower alkyl or lower alkoxy.

Another embodiment of the invention relates to pharmaceutically acceptable compositions comprised of a Formula I compound combined with at least one pharmaceutically acceptable excipient. A further embodiment of this invention relates to a method for inhibiting phosphodiesterase and blood platelet aggregation in a mammal which comprises administering a therpeutically effective amount of a compound of Formula I or a pharmaceutically acceptable salt thereof to a mammal in need of such treatment. A still further embodiment of this invention relates to a method for increasing heart inotropic activity which comprises administering a therapeutically effective amount of a compound of Formula I or a pharmaceutically acceptable salt thereof to a mammal in need of such treatment.

DETAILED DESCRIPTION OF THE INVENTION

The compounds of the instant invention comprise those of Formula I $$\text{(I)}$$

[Structure: Imidazo[4,5-b]quinoline ring system with R₂, O—Alk—Y, R₁, H, N, =O substituents]

wherein
R₁ is hydrogen, lower alkyl, benzyl;
R₂ is hydrogen, halogen, lower alkyl, lower alkoxy;
Alk is an unbranched or branched alkylene chain of 1 to 8 carbon;
Y is hydroxyl and esters thereof formed with an alkanoic acid of 1 to 6 carbon atoms or arylalkanoic acid of 7–12 carbon atoms, alkoxy wherein with Alk the number of carbon atoms ranges from 2 to 10, oxo forming a ketone, di-(lower alkyl)amino, —CO₂H, —CO₂R₃ wherein R₃ is lower alkyl;

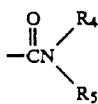

wherein R₄ is hydrogen, lower a alkyl, benzyl, cyclohexyl, —(CH₂)$_n$CO₂R₆ wherein n is the integer 1 to 8 and the alkylene chain (CH₂)$_n$ is unbranched or branched and R₆ is hydrogen or lower alkyl; R₅ is hydrogen, lower alkyl, benzyl, adamantanamyl, cycloalkyl of 3 to 7 carbon atoms wherein the cycloalkyl ring is unsubstituted or substituted with lower alkyl or lower alkoxy;

R₄ and R₅ are joined together to form morpholinyl, piperidinyl optionally substituted with —CO₂R₇ wherein R₇ is hydrogen or lower alkyl, 4-phenylpiperazinyl wherein phenyl is unsubstituted or independently substituted with up to 2 halogen, lower alkyl, or lower alkoxy groups;

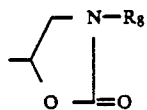

wherein R₈ is lower alkyl;

wherein R₈ is lower alkyl;

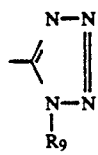

wherein R₉ is lower alkyl, cycloalkyl of 5 to 7 carbon atoms;

—SO₂—phenyl wherein phenyl is unsubstituted or independently substituted with up to 2 halogen, lower alkyl or lower alkoxy;

or a pharmaceutically acceptable salt thereof.

It is understood that as used herein limitations of Formula I are defined as follows:

The term "halogen" or "halo" comprehends fluorine, iodine, and most preferably bromine and chlorine.

The term "lower alkyl" refers to a branched or unbranched saturated hydrocarbon chain containing from 1 to 4 carbon atoms; specifically, methyl, ethyl, n-propyl, isopropyl, n-butyl, secondary butyl and tert.-butyl. The terms "alkyl of 1 to 4 carbon atoms" and "lower alkyl" are used interchangeably and specific terms may be represented by conventional symbols, i.e., Me=CH₃, Et=C₂H₅, etc.

The term "lower alkoxy" comprehends ethers containing from 1 to 4 carbon atoms as defined for alkyl; such as methoxy, ethoxy, isopropoxy, tert.-butoxy, and the like.

The term "Alk" is derived from a saturated hydrocarbon chain of 1 to 8 carbon atoms that is branched or unbranched wherein when one terminal carbon is attached to the ether oxygen and substituent A∓Y" is hydroxyl or oxo radical forming a ketone a different terminal carbon is attached thereto. Thus, substituent "Y" can be attached to the same carbon as the ether oxygen unless "Y" is hydroxy or oxo ketone.

The term "—(CH₂)$_n$CO₂R₆" comprehends alkylcarboxylic acid lower alkyl esters wherein the "—(CH₂)$_n$—" alkylene chain constitutes a divalent radical derived from a branched or unbranched alkane of 1 to 8 carbon atoms.

The terms "cycloalkyl of 3 to 7 carbon atoms" and "cycloalkyl of 5 to 7 carbon atoms" comprehends a saturated aliphatic ring containing the designated number of carbon atoms. Such radicals are, for example, cyclopropyl, cyclobutyl, cyclopentyl, cyclohexyl and cycloheptyl.

The term "SO₂—phenyl" comprehends a group wherein phenyl is unsubstituted or has one or two optional substituents selected from the group consisting of halogen lower alkyl, lower alkoxy.

The term "hydroxyl" for substituent "Y" refers to an alcohol function which can be converted to an ester by reaction with a carboxylic acid. Such an acid may be any unbranched or branched aliphatic acid 1 to 6 carbon atoms such as, for example, formic acid, acetic acid, propanoic acid, butyric acid, pentanoic acid, hexanoic acid or any isomer of these acids which has up to 6 carbon atoms and is fully saturated. In addition, the carboxylic acid may be an aryl carboxylic acid having 7 to 12 carbon atoms. Representative acids are benzoic acid, phenylacetic acid, 3-phenylpropionic acid, 4-phenylbutyric acid, 6-phenylhexanoic acid and the like.

The term "alkoxy" when used for substituent "Y" refers in combination with "Alk" to an alkyloxoalkyl group wherein the total number of carbon atoms ranges from 2 to 10 carbon and can be optionally branched when the number of carbon is 3 or more. Examples of such groups are methoxymethyl, ethoxymethyl, ethoxyethyl, propoxyethyl, isopropoxyethyl, n-heptyloxyethyl, n-butoxybutyl, isobutoxybutyl, n-heptyloxybutyl, and the like.

According to the present invention, the compounds characterized by Formula I and the pharmaceutically acceptable acid addition salts thereof are obtained by a process comprising (a) reducing a substituted hydantoin of Formula II

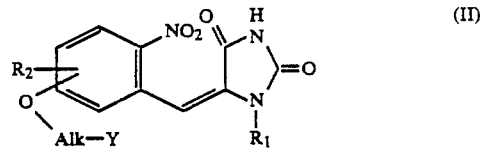

wherein Alk, R₁, R₂ and Y are defined as above, and treating the reduced material when required with an oxidant such as iodine, or (b) converting a compound of Formula III

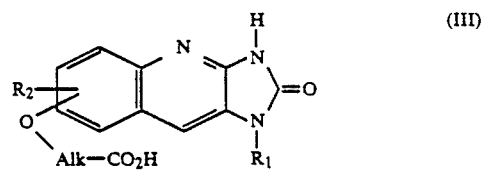

wherein Alk, R₁ and R₂ are defined as above to an amide or ester of Formula I, or (c) hydrolyzing a compound of Formula IV

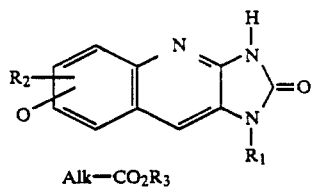

wherein Alk, $R_1$ and $R_2$ are as defined above and $R_3$ is lower alkyl to a compound of Formula I wherein Y is —$CO_2H$ characterized by Formula III;

(d) treating a compound of Formula V

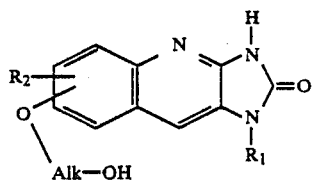

wherein Alk, $R_1$ and $R_2$ are as defined above with an alkanoic acid of 1 to 6 carbon or an arylalkanoic acid of 7-12 carbon to provide an ester thereof;

(e) reducing a compound of Formula I wherein Y is oxo forming a ketone to the corresponding alcohol;

(f) converting a compound of Formula I wherein Y is

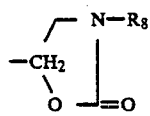

to the corresponding amino alcohol wherein Y is

(g) converting the free base of a compound of Formula I to a pharmaceutically acceptable salt is desired.

Reaction schemes illustrative of the instant process for preparing compounds of Formula I are depicted below.

SCHEME 1

(a) Reducing a substituted hydantoin of Formula II and treating the reduced material with an oxidant

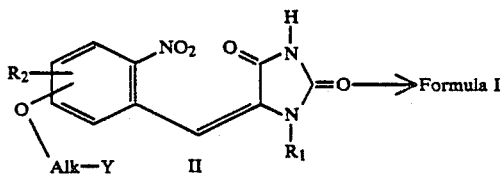

Reduction is carried out by conventional chemical or catalytic methods. For instance, the Formula II hydantoins can be chemically reduced by treatment with hydrogen iodide and red phosphorus according to the method of Kozak, et al., supra. Catalytic hydrogenation is particularly preferred and accomplished with a transition metal catalyst, preferably palladium-on-carbon, in an appropriate reaction inert solvent such as dimethylformamide (DMF). Reduction is carried out at room temperature and when hydrogen uptake is essentially complete, the reaction mixture is warmed and filtered or optionally heated to about 100° C. for a 1 to 4 hour period before filtering. In some instances, residual material (obtained by concentrating the filtrate) predominantly consists of the desired Formula I product produced by facile cyclization and aromatization to the fused quinoline ring system. In other instances, the residual material predominantly consists of the uncyclized Formula $II^a$ amino ketone

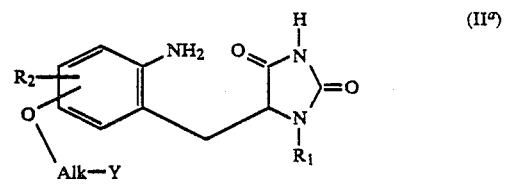

wherein $R_1$, $R_2$, Alk and Y are as defined above or the 1,3,9,9a-tetrahydroquinoline intermediate of Formula $II^b$ resulting from cyclization of $II^a$,

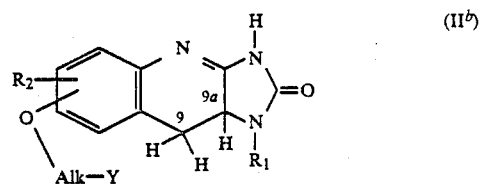

wherein $R_1$, $R_2$, Alk and Y are defined as above. In other instances, the residual material predominantly consists of a mixture of Formula $II^a$, $II^b$ intermediates together with the desired Formula I product. Without being bound by theory, the transformation of a Formula II nitro-hydantoin to the Formula I product is thought to involve reduction of the nitro group and olefinic double bond to the corresponding Formula $II^a$ amine. Ring cyclization follows or occurs simultaneously to the Formula I product or the 1,3,9,9a-tetrahydroquinoline intermediate of Formula $II^b$ which is aromatized by dehydrogenation. In those cases where reaction is incomplete, the residual material is treated with an oxidant such as iodine in an alkanol solvent such as methanol or an inert solvent such as dimethylformamide, acetonitrile and the like at reflux temperature. Under these conditions, cyclization of Formula $II^a$ amines to the Formula $II^b$ tetrahydroquinoline intermediates with oxidation of the latter to the desired 2,3-dihydro-2oxo-1H-imidazo[4,5-b]quinolinylether derivatives of Formula I is effected. The Formula $II^a$ and $II^b$ compounds along with the Formula II nitrohydantoins are considered part of the instant invention. When iodine is employed, the Formula I product is isolated in base form by treating the reaction mixture with aqueous sodium thiosulfate and alkali metal carbonate such as sodium carbonate.

In the case of Formula II compounds wherein Y is $CO_2R_3$, ester interchange can take place whenever an alcohol solvent is employed in the oxidation step. For instance, when methanol is used and "$R_3$" is not methyl, the Formula I product can consist of a mixture of the "$R_3$" and methyl esters with the latter generally predominating. The esters of Formula II (Y is $CO_2R_3$) are conventionally converted to corresponding acids by base hydrolysis. In the case of Formula II compounds wherein Y is CO₂H, esterification can take place under the relative acid conditions of the oxidation step. For instance, oxidation of the reduced product of 4-[3-(2,4-dioxoimidazolidin-5-ylidene)methyl]-4-nitrophenoxy]-butanoic acid with iodine in methanol provides methyl 4-[(2,3-dihydro-2-oxo-1H-imidazo[4,5-b]quinolin-7-yl)oxy]butanoate.

In the case of Formula II compounds wherein Y is hydroxyl, the alcoholic group can be protected, if desired, by a suitable blocking group such as 2-pyranyl or by an ester of a carboxylic acid such as acetic acid and the like. When an alkanol solvent such as methanol is used in the iodine oxidation step, the carboxylate ester is hydrolyzed providing the Formula I product wherein Y is OH. When retention of the carboxylate ester is desired, an inert solvent such as acetonitrile is employed.

In the case of Formula II compounds wherein Y is oxo, the ketonic group can be protected, if desired, by a suitable blocking group such as 1,2-dihydroxyethane to form a 1,3-dioxolane.

SCHEME 2

(b) Converting a compound of Formula III to an amide (I$^a$) or ester (IV) of Formula I

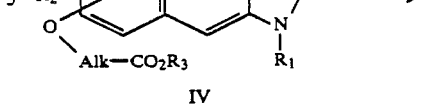

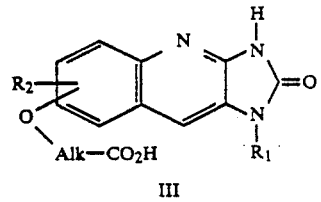

Hydrolyzing a compound of Formula IV to the corresponding acid is conventionally carried out using well known conditions and reagents; for instance, treating the Formula IV ester with a strong base for about 0.5 to 24 hours at a temperature of between 0° and 50° C. Bases which may be used to effect this reaction are

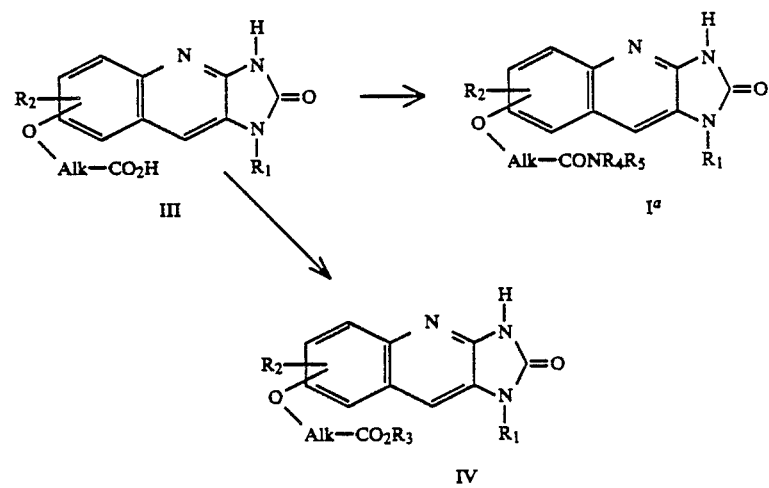

The process is conventionally carried out using well-known conditions and reagents. Thus, amides are formed by converting the Formula III acids to the acid chloride and then to the amide as described by Jones, et al., U.S. Pat. No. 4,490,371 incorporated herein by reference. An alternate and preferred amide formation process employs the Formula III acids as substrates and diphenylphosphoryl azide as a coupling reagent in dimethylformamide according to the procedure of S. Yamada, et al., J. Amer. Chem. Soc., 1972, 94, 6203–6205.

Reaction of the acid chloride of a Formula I acid with R₃OH wherein R₃ is lower alkyl affords the corresponding Formula I ester (Y is CO₂R₃) which can also be obtained from the Formula III acids by other commonly used methods such as acid catalyzed esterification.

SCHEME 3

(c) Hydrolyzing a compound of Formula IV to a compound of Formula I wherein Y is —CO₂H (characterized by Formula III)

preferably alkali metal bases such as sodium hydroxide, potassium hydroxide and the like. Generally, the reaction will be allowed to proceed for about 2 hours at room temperature to provide an alkali salt of the acid which can be neutralized, if desired, by acidification with an acid such as hydrochloric acid to provide the free acid.

SCHEME 4

(d) Treating a compound of Formula V with an alkanoic acid of 1 to 6 carbon atoms or arylalkanoic acid of 7–12 carbon atoms to provide an ester thereof (characterized by Formula I$^b$ wherein R₁₀ corresponds to the carboxylate radical of the selected acid)

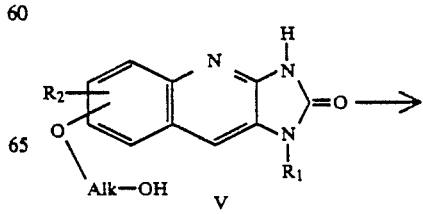

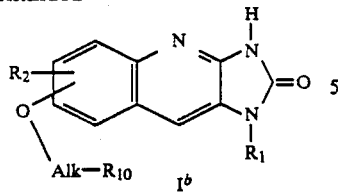

Treating a compound of Formula V with an acid to provide an ester is effected by conventional methods. For instance, reaction of 1,3-dihydro-7-(3-hydroxypropoxy)-2H-imidazo[4,5-b]quinolin-2-one with butyryl chloride in an inert solvent such as tetrahydrofuran, chloroform, dioxane, dimethylformamide and the like affords methyl 3-[(2,3-dihydro-2-oxo-1H-imidazo[4,5-b]quinolin-7-yl)oxo]propyl butanoate.

SCHEME 5

(e) Reducing a compound of Formula I wherein Y is oxo forming ketone (characterized by Formula $I^c$ wherein $R_{11}$ is oxo) to the corresponding alcohol (characterized by Formula $I^d$ wherein $R_{12}$ is OH)

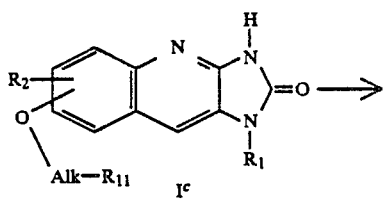

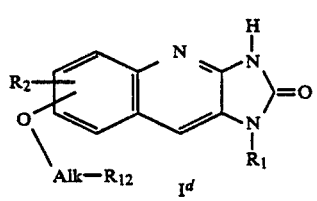

The reaction is carried out by conventional catalytic or chemical methods and preferably with sodium borohydride in an inert solvent such as dimethylformamide.

With reference to the above process "(f) converting a compound of Formula I wherein Y is

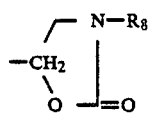

to the corresponding amino alcohol wherein Y is

the reaction is carried out by base (e.g. sodium hydroxide) catalyzed hydrolysis of the cyclized carbamate.

With reference to the above process "(g) converting the free base of a compound of Formula I to a pharmaceutically acceptable salt thereof", conventional methods are used. For instance, pharmaceutically acceptable salts of Formula I are obtained by treating a Formula I base with the selected acid preferably in solution. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from one retention of an ion exchange resin. The pharmaceutically acceptable acid addition salts of the instant invention are those in which the anion does not contribute significantly to the toxicity or pharmacological activity of the salt and, as such, they are the pharmacological equivalents of the bases of Formula I. They are generally preferred for medical usage. In some instances, they have physical properties which make them more desirable for pharmaceutical formulation purposes such as solubility, lack of hygroscopicity, compressibility with respect to tablet formation and compatibility with other ingredients with which the substance may be used for pharmaceutical purposes. Pharmaceutically acceptable acids for the purposes of salt formation of the substances of Formula I include hydrochloric, hydrobromic, hydroiodic, citric, acetic, propionic, benzoic, mandelic, sulfuric, phosphoric, nitric, mucic, isethionic, methanesulfonic, ethanesulfonic, p-toluene sulfonic, palmitic, heptanoic, and others.

In the case of compounds of Formula I wherein Y is $-CO_2H$, pharmaceutically acceptable metal salts, particularly the alkaline earth or alkali metal salts (preferably sodium and potassium) are useful and are prepared by conventional techniques such as evaporating an equimolar mixture of the Formula I acid and sodium methylate in methanol.

The Formula II hydantoins employed in the process for preparing compounds of Formula I can be prepared according to procedures described by Billek, Montash, 1961, 92, 352–360 (Chem. Abs., 1962, 56, 394b) illustrated in the following reaction scheme.

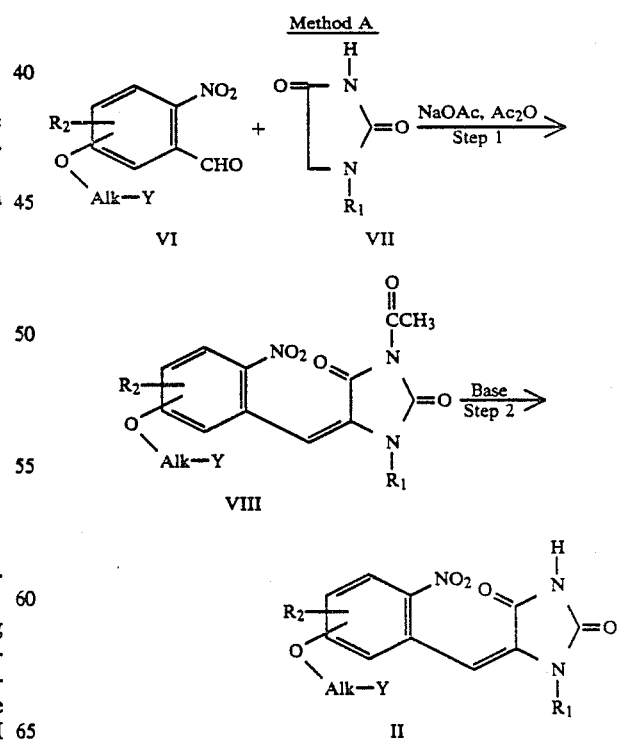

Method A involves condensation of a substituted benzaldehyde of Formula VI with hydantoin (VII) in the presence of fused sodium acetate in acetic anhydride at elevated temperatures (e.g., 100°–160° C.). Hydrolysis of the N-acetyl intermediate (VIII) obtained in Step 1 is conventionally carried out with an alkali metal hydroxide such as sodium hydroxide to provide the benzylidine hydantoin of Formula II.

An alternate and preferred method for preparing Formula II hydantoins involves reaction of the 2-nitrobenzaldehyde of Formula VI with a hydantoin-5-phosphonate of Formula IX (wherein $R_1$ is hydrogen or lower alkyl) illustrated in the following reaction scheme.

METHOD B

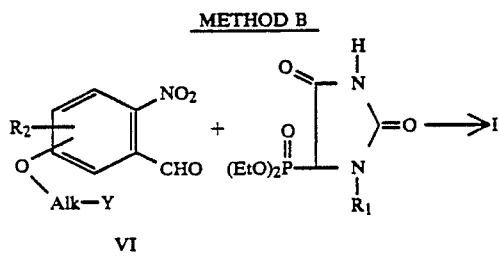

VI

The reaction is conveniently carried out at room temperature by adding the phosphonate (IX) to a molar equivalent of sodium dissolved in an alkanol solvent such as ethanol followed by addition of the benzaldehyde (VI). Alternatively, phosphonate (IX) can be added to an organic base such as triethylamine in a solvent such as acetonitrile at room temperature. A relatively short period of time is required to complete the reaction (e.g. 0.5 to 2 hours) and the hydantoin (II) is isolated by concentrating the reaction mixture and washing the residue with water. The benzylidine hydantoin derivatives (II) thus obtained frequently consist of a mixture of geometrical isomers wherein the predominate isomer has the vinyl proton (where present) resonating at lower field in the NMR spectrum. In the instant process for preparing Formula I compounds from hydantoins (II), it is immaterial as to which isomer is used since the double bond is reduced.

Jones, et al., supra., incorporated herein by reference, describes preparation of compounds of Formula VI wherein Y is $CO_2H$ (acid), $CO_2R_3$ (ester), and $CONR_4R_5$ (amide). In general, the procedure comprises alkylation of the appropriate hydroxy-2-nitrobenzaldehyde with a bromo alkanoate followed by alkaline hydrolysis of the ester to the acid. Amides of Formula (VI) are prepared by the Jones, et al., supra., acid chloride method or preferably by the carbonic anhydride method of Anderson, et al., *J. Amer. Chem. Soc.*, 1967, 89, 5012–5017.

The Formula (IX) phosphonates are prepared by brominating the appropriate $R_1$-imidazolidine-2,4-dione and coupling the product with triethylphosphite as set forth in the following typical preparation of diethyl 1-methyl-2,4-dioxoimidazolidine-5-phosphonate and analogs.

A mixture of 1-methylimidazolidine-2,4-dione (202.5 g, 1.8M) and glacial acetic acid (1 L) was heated to 90° C. in an oil bath. An addition funnel was charged with bromine (311.5 g, 100 mL, 1.95M) and a small amount of bromine introduced into the reaction mixture. After dissipation of the orange color, the remainder of the bromine was added dropwise at such a rate that instant decolorization occurred. After completing the addition, the mixture was stirred at 90° C. for 60 minutes, cooled to room temperature and stirred overnight. The acetic acid was decanted from a white precipitate, concentrated in vacuo and the residue combined with the precipitate and suspended in diethyl ether (approximately 2 L). Triethyl phosphite (295 g, 320 mL, 1.8M) was added portionwise with stirring. An exothermic reaction ensued which was controlled with tap water cooling of the reaction vessel. A solution resulted which, on continued stirring, yielded a white precipitate. After standing for 60 minutes the mixture was poured into diethyl ether (4 L) and allowed to stand overnight. Filtration afforded diethyl-1-methyl-2,4-dioxoimidazolidine-5-phosphonate (331.7 g, 75%), m.p. 95°–96° C. An analytical sample crystallized from MeOH/Et$_2$O had m.p. 95°–95° C.

Anal. Calcd. for $C_8H_{15}N_2O_5P$: C, 38.41; H, 6.04; N, 11.20. Found: 38.22; H, 6.07; N, 11.04.

The following 5-phosphonate hydantoin intermediates can be prepared analogously by substituting the appropriate imidazolidine-2,4-dione for 1-methylimidazolidine-2,4-dione in the above procedure:
diethyl 2,4-dioxoimidazolidine-5-phosphonate, m.p. 161°–163° C. crystallized from ethanol,
diethyl 1-ethyl-2,4-dioxoimidazolidine-5-phosphonate,
diethyl 1-propyl-2,4-dioxoimidazolidine-5-phosphonate,
diethyl 1-isopropyl-2,4-dioxoimidazolidine-5-phosphonate,
diethyl 1-butyl-2,4-dioxoimidazolidine-5-phosphonate,
diethyl 1-iso-butyl-2,4-dioximidazolidine-5-phosphonate,
diethyl 1-tert-butyl-2,4-dioxoimidazolidine-5-phosphonate.

As stated above, the Formula I compounds or pharmaceutically acceptable salts thereof have pharmacological properties which make them particularly useful as phosphodiesterase inhibitors, blood platelet antiaggregators and/or cardiotonic agents. Regarding the latter, compounds of the invention selectively strengthen myocardial contraction force by which the heart ventricles pump blood into the periphery. Thus, the instant compounds are useful in the curative or prophylactic treatment of cardiac conditions such as myocardial failure where an increase in positive inotropic activity is desirable. Preferred compounds increase contractile force without unduly increasing heart rate.

Platelet aggregation is considered part of a complex physiological mechanism for formation of a thrombus in the vascular system. Thromboembolic phenomena, i.e., the formation of thrombi, are involved in hemostasis and a number of diseased states in mammals including thrombophlebitis, phlebothrombosis, cerebral thrombosis, coronary thrombosis and retinal vessel thrombosis. An increase in propensity for platelet aggregation, sometimes referred to as platelet adhesiveness, is observed following parturition, surgical operations such as coronary artery bypass surgery, organ transplant, angioplasty, prosthetic heart valve implants to name a few; and in ischaemic heart disease, atherosclerosis, multiple sclerosis, intracranial tumors, thromboembolism, and hyperlipemia; refer to A. Poplawski, et al., *J. Atherosclerosis Research*, 8, 721 (1968). Thus, the compounds of the invention which have antithrombogenic (inhibit blood platelet aggregation) and phosphodiesterase inhibition properties are useful in prevention or treatment of conditions involving platelet aggregation and thrombosis such as the above. Literature relating to prophylactic and therapeutic activities of phosphodiesterase inhibiting compounds include the following: S. M. Amer, "Cyclic Nucleotides as Targets For Drug Design," *Advances in Drug Research*, Vol. 12, 1977, Academic Press, London, pp 1–38; I. Weinryh, et al., *J. Pharm. Sci.*, pp 1556–1567 (1972); S. M. Amer, et al., *J. Pharm. Sci.*, Vol. 64, pp 1–37 (1975); and D. N. Harris, et al., *Enzyme Inhibitors As Drugs*, McMillan & Co., Ed-M. Standler, pp 127–146, (1980). The instant compounds are considered to have antimetastatic potential in view of their platelet inhibition properties.

The pharmacological properties of the instant compounds can be demonstrated by conventional in vitro and in vivo biological tests such as the following.

IN VITRO INHIBITION OF PLATELET AGGREGATION

The aggregometer method of Born (1), as modified by Mustard, et al. (2) was used to assess the in vitro activity of the various compounds as to inhibition of adenosine diphosphate (ADP) and collagen-induced platelet aggregation. Platelet rich plasma (PRP) was separated by centrifugation from citrated (3.8 percent) rabbit blood. ADP in final concentration of 0.5 mcg/ml or 0.05 ml of a collagen suspension prepared according to the method described by Evans, et al. (3) was used to induce aggregation. The various compounds tested were dissolved in dimethylsulfoxide (DMSO) so that 5 mcl added to the platelet rich plasma would yield the desired test concentration. Vehicle control trials were done and compared with aggregation induced in platelet rich plasma containing various concentrations of the test compounds. Dose response curves were obtained and Effective Concentration (EC50) values calculated. In this test, the $EC_{50}$ values for dipyridamole, a clinically useful antithrombogenic agent, are >512 mcg/ml vs. ADP and 245 mcg/ml vs. collagen. Results are given in Table I hereinafter for various Formula I compounds.

1. Born, G. V. R., J. Physiol., London, 162, 67P (1962).
2. Mustard, J. F., Hegardt, B. Rowsell, H. C. and MacMillan, R. L., J. Lab. Clin. Med., 64, 548 (1964).
3. Evans, G., Marian M. C., Packham, M. A., Nishizawa, E. E., Mustard, J. F. and Murphy, E. A., J. Exp. Med., 128, 877 (1968).

INHIBITION OF PLATELET AGGREGATION FOLLOWING ORAL ADMINISTRATION

This test is sometimes referred to in the art as an Ex vivo method and was initially described by Fleming, et al., *Arch. Int. Pharmacodyn. Ther.*, 199, 164 (1972). Briefly, the assay is essentially carried out as follows.

Aggregometry is performed in vitro as previously described on platelet rich plasma samples obtained from rats dosed with either test compounds or the vehicle. In all cases, activity is determined 2 hours after the drug is administered orally at various doses by gavage as a suspension in 0.9% water plus a few drops of Tween 20. Drug activity is expressed as $ED_{50}$'s (that dose required to inhibit the induced aggregation by 50%) calculated from results obtained from groups of 10 animals treated with various doses of test compounds in comparison to separate control groups.

In this test, the $ED_{50}$ of dipyridamole is greater than 100 mg/kg and anagrelide is 4.9 mg/kg. Results are given in Table I hereinafter for various Formula I compounds.

INHIBITION OF CYCLIC AMP PHOSPHODIESTERASE

This assay is carried out essentially as described by Thompson, et al., *Methods in Enzymology*, 38, 205–212 (1974). Briefly, tritium labeled cyclic adenosine monophosphate (cAMP) is incubated with a phosphodiesterase (PDE) enzyme obtained from human platelets which converts a portion of the cAMP to 5'AMP in culture tubes. This reaction is terminated by submerging the tubes in a boiling water bath after which they are placed on ice and an aliquot of snake venom is added to each tube. This, during a second incubation, converts the 5'AMP to adenosine. Ion exchange resin is added to bind the remaining cyclic AMP. The tubes are centrifuged to sediment the resin and a portion of the clear supernatent (which contains radioactive adenosine) is counted in a liquid scintillation counter. The cAMP phosphodiesterase inhibition activity of a test agent is determined by pre-incubating the PDE enzyme preparation with the test agent. Dose response values are obtained and activity of the test agent reported as the molar (M) concentration of the test agent inhibiting 50% of the PDE activity ($IC_{50}$s). In this test, the $IC_{50}$ value of milrinone, a known inotropic agent, is $2 \times 10^{-7}$ molar. Results are given in Table I hereinafter for various Formula I compounds.

IN VIVO INOTROPIC ACTIVITY

This test is carried out in ferrets as follows.

Fasted anesthetized ferrets are instrumented to study hemodynamic parameters as well as right ventricular contractile force (RVCF) using a Walton-Brodie open strain guage arch. Drugs are administered intraduodenally as solutions in DMSO (1 mL or less) and effects on myocardial contractile force and other parameters are monitored for 60 minutes after dosing. Changes in contractile force in response to drug treatment are expressed in terms of percent change from predose control.

In this test, milrinone produces a 52% increase in RVCF at 3 mg/kg. Results are given in Table II hereinafter for various Formula I compounds.

TABLE I

| | Inhibition of Platelet Aggregation and cAMP Phosphodiesterase | | | |
|---|---|---|---|---|
| | Platelet Inhibition In Vitro - Rabbit PRP $EC_{50}$ (mcg/ml) | | Ex Vivo vs. ADP $ED_{50}$ | cAMP Phosphodiesterase Human Platelets |
| Example[a] | vs. ADP | vs. collagen | (mg/kg) | $IC_{50}(M)$ |
| 4 | 0.3 | 0.1 | 3.4 | $5 \times 10^{-9}$ |
| 6 | >32 | >32 | | $6 \times 10^{-7}$ |
| 8 | >32 | >32 | | $5 \times 10^{-9}$ |
| 9 | >32 | >32 | | $8 \times 10^{-7}$ |
| 7 | | | | $7 \times 10^{-8}$ |
| 10 | 0.02 | 0.006 | 4.4 | $4 \times 10^{-7}$ |
| 11 | 0.6 | 0.08 | 15.7 | $7 \times 10^{-6}$ |
| 13 | 0.3 | 0.03 | >10 | $3 \times 10^{-8}$ |
| 14 | 3 | 0.2 | | $5 \times 10^{-6}$ |
| 12 | 8 | 2.5 | | $2 \times 10^{-6}$ |
| 30 | 0.002 | 0.001 | 2.4 | $2 \times 10^{-9}$ |
| 31 | 0.02 | 0.018 | 2.1 | $2 \times 10^{-7}$ |
| 32 | 0.003 | 0.0008 | 3.8 | $2 \times 10^{-9}$ |
| 27 | 0.06 | 0.03 | | $5 \times 10^{-7}$ |
| 22 | 0.007 | 0.002 | 6.2 | $3 \times 10^{-9}$ |
| 23 | 0.03 | 0.005 | | $3 \times 10^{-5}$ |
| 33 | 0.002 | 0.0006 | 1.7 | $4 \times 10^{-10}$ |
| 28 | 0.06 | 0.03 | | $6 \times 10^{-7}$ |
| 21 | 0.0025 | 0.0008 | <3 | $5 \times 10^{-10}$ |
| 24 | 0.04 | 0.03 | | $2 \times 10^{-8}$ |
| 25 | 4.0 | 0.8 | | $2 \times 10^{-6}$ |

TABLE I-continued

Inhibition of Platelet Aggregation and cAMP Phosphodiesterase

| Example[a] | Platelet Inhibition In Vitro - Rabbit PRP $EC_{50}$ (mcg/ml) vs. ADP | vs. collagen | Ex Vivo vs. ADP $ED_{50}$ (mg/kg) | cAMP Phosphodiesterase Human Platelets $IC_{50}(M)$ |
|---|---|---|---|---|
| 16 | 0.05 | 0.02 | 4.0 | $1 \times 10^{-9}$ |
| 18 | 0.015 | 0.0025 | <10 | $3 \times 10^{-8}$ |
| 19 | 0.07 | 0.009 | 8.3 | $7 \times 10^{-7}$ |
| 15 | 0.1 | 0.007 | >10 | $4 \times 10^{-8}$ |
| 26 | 0.125 | 0.009 |  | $2 \times 10^{-9}$ |
| 36 | 0.11 | 0.02 | >10 | $4 \times 10^{-9}$ |
| 35 | 0.07 | 0.03 | 4.3 | $1 \times 10^{-9}$ |
| 34 | 1.5 | 0.4 |  | $3 \times 10^{-7}$ |
| 41 | 3.0 | 7.0 |  | $6 \times 10^{-8}$ |
| 42 | 6.0 | 0.4 |  | $7 \times 10^{-8}$ |
| 43 | >32 | >32 |  | $3 \times 10^{-7}$ |

[a] Refer to examples below for compound identification.

TABLE II

Ferret In Vivo Inotropic Activity Maximum Percentage Change Following Intraduodenal Administration

| Example[a] | Dose (mg/kg) | Right Ventricular Contractile Force | Blood Pressure | Number of Animals |
|---|---|---|---|---|
| 4 | 3 | 3 ± 5 | −3 ± 2 | 3 |
| 10 | 3 | −9 ± 1 | −14 ± 8 | 3 |
|  | 0.3 | 9.0 ± 10 | −14 ± 9 | 3 |
| 11 | 3 | −10 | −4 | 1 |
| 30 | 3 | 35 ± 2 | −30 ± 2 | 2 |
| 30 | 0.3 | 41 ± 5 | −27 ± 6 | 3 |
| 30 | 0.03 | 8 ± 2 | −3 ± 0 | 2 |
| 31 | 3 | 3 ± 6 | −36 ± 3 | 3 |
| 31 | 0.3 | 0 ± 6 | −28 ± 5 | 3 |
| 32 | 0.3 | 18 ± 4 | −27 ± 10 | 3 |
| 27 | 3 | 35 | −24 | 1 |
| 22 | 0.3 | 29 ± 5 | −26 ± 4 | 3 |
| 23 | 3 | 24 | −16 | 1 |
| 33 | 0.3 | 27 ± 8 | −34 ± 2 | 3 |
| 28 | 3 | 27 | −12 | 1 |
| 21 | 3 | 26 | −26 | 1 |
| 24 | 3 | 32 | −19 | 1 |
| 16 | 3 | 6 ± 3 | −10 ± 4 | 3 |
| 18 | 3 | 5 | −8 | 1 |
| 15 | 3 | 2 | −5 | 1 |
| 35 | 3 | 11 ± 5 | −10 ± 8 | 3 |

[a] Refer to examples below for compound identification.

As stated above, one aspect of this invention relates to a therapeutic method for inhibiting phosphodiesterase and blood platelet aggregation in a mammal which comprises administering a therapeutically effective amount of a compound of Formula I or a pharmaceutically acceptable salt thereof to a mammal ia need of such treatment. Another aspect of this invention as stated above relates to a theraputic method for increasing heart inotropic activity which comprises administering to a warm-blooded animal, including man, in need of such treatment a therapeutically effective amount of a compound of Formula I, preferably a compound selected from the group consisting of N-cyclohexyl-N-methyl-4-[(2,3-dihydro-2-oxo-1H-imidazo[4,5-b]quinolin-7-yl)oxy]butanamide N-cyclohexyl-N-methyl-5-[(2,3-dihydro-2-oxo-1H-imidazo[4,5-b]quinolin-7-yl)oxo]pentanamide N-cyclohexyl-5-[(2,3-dihydro-1-methyl-2-oxo-1H-imidazo[4,5-b]quinolin-7-yl)oxy]-N-methylpentanamide N-cycloheptyl-N-methyl-4-[(2,3-dihydro-2-oxo-1H-imidazo[4,5-b]quinolin-7-yl)oxy]butanamide N-cycloheptyl-4-[(2,3-dihydro-1-methyl-2-oxo-1H-imidazo[4,5-b]quinolin-7-yl)oxy]-N-methylbutanamide N-cycloheptyl-N-methyl-5-[(2,3-dihydro-2-oxo-1H-imidazo[4,5-b]quinolin-7-yl)oxy]pentanamide N-cycloheptyl-5-[(2,3-dihydro-1-methyl-2-oxo-1H-imidazo[4,5-b]quinolin-7-yl)oxy]-N-methylpentanamide N-cyclohexyl-N-[4-[(2,3-dihydro-2-oxo-1H-imidazo[4,5-b]quinolin-7-yl)oxy]-1-oxobutyl]glycine methyl ester 1-[4-[(2,3-dihydro-2-oxo-1H-imidazo[4,5-b]quinolin-7-yl)oxy]-1-oxobutyl]piperidine.

The dosage employed in the instant therapeutic methods will vary with the form of administration, the particular compound chosen, the subject being tested and the effect desired. Suitable effective doses in animals range from 0.5–30 mg/kg body weight orally and from 0.05–10 mg/kg body weight parenterally (generally characterized as subcutaneous, intramuscular, and intravenous injection). It is contemplated that the effective unit dose in man will range from 0.1 to 30 mg. and preferably from 0.5 to 20 mg. administered one to three times a day. In accordance with conventional clinical practice, the effective dose can be determined by administering a Formula I compound at a dosage substantially less than the dose of the compound which is thought to be effective and then increasing the dosage in small increments until the desired effect is achieved.

In carrying out the instant therapeutic methods, the active ingredient of Formula I and pharmaceutically acceptable acid addition salts thereof are preferably administered with a pharmaceutically acceptable carrier and such compositions constitute part of the instant invention. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutical acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated or coated by known techniques to delay disintegration and absorption in the gastrointestinal tract and thereby provide a sustained action over a longer period. Similarly, suspension, syrups and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectible compositions are formulated as known in the art and may contain appropriate dispersing or wetting agents and suspending agents identical or similar to those mentioned above.

The following examples are given by way of illustration and are not to be construed as limiting the invention in any way inasmuch as many variations of the invention are possible within the spirit of the invention. All temperatures are degrees Centrigrade and melting points taken with a Thomas Hoover capillary apparatus are uncorrected. Conventional abbreviations are employed in reporting Nuclear Magnetic Resonance (NMR) spectral data with tetramethylsilane as internal reference and chemical shift data values in parts per million.

EXAMPLE 1

METHOD A

Preparation of Hydantoin Intermediates of Formula II by Condensation of 2-Nitrobenzaldehydes (VI) With Hydantoins (VII) by Adaptation of the Method of Billek, *Montash Chem.*, 92, 352–360 (1961)

(1-1)

5-[[5-[3-[[(Cyclohexyl)methylamino]carbonyl]propoxy]-2-nitrophenyl]methylene]imidazolidine-2,4-dione A mixture of N-cyclohexyl-4-(3-formyl-4-nitrophenoxy)-N-methylbutanamide (20 g, 57 mmol), hydantoin (5.75 g, 57 mmol), sodium acetate (4.71 g, 57 mmol) and acetic anhydride (110 mL) was heated to reflux under an atmosphere of argon. After 45 minutes, the mixture was cooled and diluted with water (40 mL) producing an exothermic reaction. The mixture was cooled in an ice bath and additionally diluted with water (150 mL) added portionwise over 5 minutes. The mixture was extracted with dichloromethane (4×250 mL), the combined extracts dried over sodium sulfate and concentrated in vacuo. The residue was dissolved in a mixture of methanol (150 mL) and 4N sodium hydroxide solution (300 mL). After 30 minutes, the reaction mixture was acidified with 6N hydrochloric acid solution and the brown precipitate filtered off, washed with water and dried in air to give 5-[[5-[3-[[(cyclohexyl)methylamino]carbonyl]propoxy]-2-nitrophenyl]methylene]imidazlidine-2,4-dione (20.55 g, 83%). An analytical sample was purified by dissolving in ethyl acetate and adding enough hexane to precipitate some tarry material. After decanting, further dilution with hexane afforded pure material as a partial hydrate with an indistinct melting point.

Anal. Calcd. for $C_{21}H_{26}N_4O_6 \cdot 0.1H_2O$: C, 58.35; H, 6.11; N, 12.96; $H_2O$, 0.42. Found: C, 58.85; H, 6.24; N, 12.27; $H_2O$, 0.57.

(1-2)

4-[[4-Nitro-3-[(2,4-dioxoimidazolidin-5-ylidene)methyl]phenyl]oxy]butanoic acid

A mixture of ethyl 4-[3-formyl-4-nitrophenoxy]butanoate (2.00 g, 7.1 mmol), hydantoin (0.71 g, 7.1 mmol), and anhydrous sodium acetate (0.58 g, 7.1 mmol) and acetic anhydride (20 mL) was heated at reflux for 1 hour. Upon cooling, $H_2O$ was added and the mixture extracted with dichloromethane. The organic portion was washed with water, evaporated, and the residue dissolved in a solution of methanol (20 mL) and 4N NaOH (30 mL). After stirring for 1 hour, the mixture was acidified to pH=2 by addition of 2N HCl. The precipitate was collected and triturated with MeOH/$CH_2Cl_2$ to afford 4-[[4-nitro-3-[(2,4-dioxoimidazolidin-5-ylidene)methyl]phenyl]oxy]butanoic acid (0.88 g, 37%). An analytical sample was prepared by crystallization from DMF/$H_2O$ to give gold plates, m.p. 181°–184° C.

Anal. Calcd. for $C_{14}H_{13}N_3O_7$: C, 50.15; H, 3.91; N, 12.53. Found: C, 50.27; H, 3.89; N, 12.54.

(1-3)

5-[[4-Nitro-3-[(2,4-dioxoimidazilidin-5-ylidene)methyl]phenyl]oxy]pentanoic Acid Prepared from ethyl 4-[3-formyl-4-nitrophenoxy]pentanoate and hydantoin analogous to the procedure of Example (1-2), m.p. 191°–193° C.

Anal. Calcd. for $C_{15}H_{15}N_3O_7$: C, 51.58; H, 4.33; N,, 12.03. Found: C, 51.34; H, 4.30; N, 11.89.

(1-4)

N-Cyclohexyl-N-methyl-5-[3-[(2,4-dioxoimidazolidin-5-ylidene)methyl]-4-nitrophenoxy]pentanamide Prepared as a partial hydrate, m.p. 104°–108° C., from N-cyclohexyl-4-(3-formyl-4-nitrophenoxy)-N-methylpentanamide and hydantoin analogous to the procedure of Example (1-1).

Anal. Calcd. for $C_{22}H_{28}N_4O_6 \cdot 0.6H_2O$: C, 58.04; H, 6.46; N, 12.31; $H_2O$, 2.37. Found: C, 58.28; H, 6.52; N, 12.07; $H_2O$, 2.52.

(1-5)

N-Cycloheptyl-N-methyl-5-[[4-nitro-3-(2,4-dioxoimidazolidin-5-yl)methylene]phenoxy]pentanamide Prepared as a partial hydrate, m.p. 122°–126° C., from N-cycloheptyl-4-(3-formyl-4-nitrophenoxy-N-methylpentanamide and hydantoin analogous to the procedure of Example (1-1).

Anal. Calcd. for $C_{23}H_{30}N_4O_6 \cdot 0.75H_2O$: C, 58.53; H, 6.73; N, 11.87; $H_2O$, 2.86. Found: C, 58.18; H, 6.79; N, 11.59; $H_2O$, 2.76.

EXAMPLE 2

METHOD B

Preparation of Hydantoin Intermediate of Formula II by Condensation of 2-Nitrobenzaldehyde (VI) With Hydantoin-5-phosphonate (IX)

(2-1)

Ethyl 4-[3-[(2,4-dioxoimidazolidin-5-ylidene)methyl]-4-nitrophenoxy]butanoate

Sodium (4.92 g, 0.21 g atom) was dissolved in absolute ethanol (600 mL) and diethyl 2,4-dioxoimidazolidine-5-phosphonate (50.5 g, 0.21 mole) added. After 10 minutes, a solution of ethyl 4-(3-formyl-4-nitrophenoxy)butanoate (50.0 g, 0.18 mole) in ethanol (100 mL) was added in one portion. The mixture was stirred for 2 hours, concentrated in vacuo to about 250 mL and diluted with water. After 20 minutes the precipitate was filtered off. Two further crops were subsequently collected from mother liquors. Combined solids were dried in vacuo over $P_2O_5$ to afford ethyl 4-[3-[(2,4-dioxoimidazolidin-5-ylidene)methyl]-4-nitrophenoxy]butanoate (61.3 g, 95%) which by NMR was a 4:1 mixture of geometrical isomers. An analytical sample of the major isomer was obtained by crystallization from aqueous ethanol and had m.p. 131°–134° C.

Anal. Calcd. for $C_{16}H_{17}N_3O_7$: C, 52.89; H, 4.72; N, 11.57. Found: C, 52.94; H, 4.71; N, 11.57.

(2-2)

Ethyl [3-[(2,4-Dioxoimidazolidin-5-yl-idene)methyl]-4-nitrophenoxy]acetate

Prepared from diethyl 2,4-dioxoimidazolidine-5-phosphonate and ethyl 4-(3-formyl-4-nitrophenoxy)acetate analogous to the procedure of Example (2-1), m.p. 268°–270° C.

Anal. Calcd. for $C_{14}H_{13}N_3O_7$: C, 50.16; H, 3.91; N, 12.54. Found: 50.06; H, 3.89; N, 12.51.

(2-3)

Ethyl 5-[3-[(2,4-Dioxoimidazolidin-5-ylidene)methyl]-4-nitrophenoxy]pentanoate

Prepared from diethyl 2,4-dioxoimidazolidine-5-phosphonate and ethyl 4-(3-formyl-4-nitrophenoxy)pentanoate analogous to the procedure of Example (2-1), m.p. 127°–129° C.

Anal. Calcd. for $C_{17}H_{19}N_3O_7$: C, 54.11; H, 5.08; N, 11.14. Found: C, 54.28; H, 5.14; N, 11.29.

(2-4)

Ethyl 4-[3-[(1-Methyl-2,4-dioxoimidazolidin-5-ylidene)methyl]-4-nitrophenoxy]butanoate

Prepared from diethyl 1-methyl-2,4-dioxoimidazolidine-5-phosphonate and 4-(3-formyl-4-nitrophenoxy)butanoate analogous to the procedure of Example (2-1), m.p. 161°–163° C.

Anal. Calcd. for $C_{17}H_{19}N_3O_7$: C, 54.11; 5.08; N, 11.14. Found: C, 54.01; H, 5.08; N, 11.12.

(2-5)

Ethyl 5-[3-[(1-Methyl-2,4-dioxoimidazolidin-5-ylidene)methyl]-4-nitrophenoxy]pentanoate

Prepared from diethyl 1-methyl-2,4-dioxoimidazolidine-5-phosphonate and ethyl 4-(3-formyl-4-nitrophenoxy)pentanoate analogous to the procedure of Example (2-), m.p. 121°–123° C.

Anal. Calcd. for $C_{18}H_{21}N_3O_7$: C, 55.24; H, 5.41; N, 10.74. Found: C, 55.22; H, 5.47; N, 10.80.

(2-6)

N-Cyclohexyl-N-methyl-4-[3-[(1-methyl-2,4-dioxoimidazolidin-5-ylidene)methyl]-4-nitrophenoxy]butanamide

Sodium (0.079 g, 0.003 g atom) was dissolved in ethanol (20 mL) and diethyl 1-methyl-2,4-dioxoimidazolidine-5-phosphonate (0.86 g, 3.4 mmol) added. After 5 minutes, N-cyclohexyl-4-(3-formyl-4-nitrophenoxy)-N-methylbutanamide (1 g, 2.9 mmol) was added and the mixture stirred at room temperature for 90 minutes. The solvent was evaporated and the residue diluted with water and extracted with dichloromethane to give a foam. Crystallization from hexane/dichloromethane afforded N-cyclohexyl-N-methyl-4-[3-[(1-methyl-2,4-dioxoimidazolidin-5-ylidene)methyl]-4-nitrophenoxy]butanamide (0.96 g, 75%) as a 3:1 mixture of geometrical isomers, m.p. 149°–154° C.

Anal. Calcd. for $C_{22}H_{28}N_4O_6$: C, 59.45; H, 6.36; N, 12.61. Found: C, 59.27; H, 6.29; N, 12.44.

(2-7)

5-[[5-[4-(1-Cyclohexyl-1H-tetrazol-5-yl)butoxy]-2-nitrophenyl]methylene]-2,4-imidazolidinedione

Sodium (1.38 g, 0.06 g atom) was dissolved in ethanol (250 mL) and diethyl 2,4-dioxoimidazolidine-5-phosphonate (14.22 g, 60 mmol) added. After 5 minutes, a solution of 5-[4-(1-cyclohexyl-1H-tetrazol-5-yl)butoxy]-2-nitrobenzaldehyde (17.30 g, 46 mmol) obtained according to T. Nishi, et al., Chem. Pharm. Bull., 33, 1140–1147 (1985) in ethanol (50 mL) and dichloromethane (50 mL) was added in one portion. This mixture was stirred for 10 minutes, the solvent evaporated and the residue diluted with wter and 2N hydrochloric acid solution. The yellow precipitate was filtered off, washed with water and dried in air to give 5-[[5-[4-(1-cyclohexyl-1H-tetrazol-5-yl)butoxy]-2-nitrophenyl]methylene]-2,4-imidazolidinedione (18.38 g, 87%). an analytical sample (as a partial hydrate) was prepared by crystallization from aqueous dimethylformamide and had m.p. indistinct.

Anal. Calcd. for $C_{21}H_{25}N_7O_5 \cdot 0.2H_2O$: C, 54.95; H, 5.58; N, 21.36; $H_2O$, 0.79. Found: C, 54.78; H, 5.74; N, 21.08; $H_2O$, 0.86.

(2-8)

5-[[2-Nitro-5-[4-(phenylsulfonyl)butoxy]phenyl]methylene]-2,4-imidazolidinedione

Sodium (0.386 g, 0.017 g, atom) was dissolved in ethanol (70 mL) and diethyl 2,4-dioxoimidazolidine-5-phosphonate (3.96 g, 17 mmol) added. After 1 hour, a solution of 2-nitro-5-[4-(phenylsulfonyl)butoxy]benzaldehyde (4.70 g, 13 mmol) (prepared by alkylating 5-hydroxy-2-nitrobenzaldehyde with 4-phenylsulfonylbutyl bromide) in ethanol and chloroform was added. After 20 minutes, the solvent was evaporated and the residue extracted with chloroform to give a foamy solid which was dissolved in acetontirile. Diethyl ether was added to the point of precipitate nd the mixture allowed to stand overnight. A solid (0.86 g) was collected and further purified gy crystallization from acetonitrile-diethyl ether to give 5-[[2-nitro-5-[4-(phenylsulfonyl)butoxy]phenyl]methylene]-2,4-imidazolidinedione (0.5 g). Concentration of the combined mother liquors afforded 4.1 g of material that was used without further purification. Yield (4.6 g, 61%). Crystallized material had m.p. 150°–152° C.

Anal. Calcd. for $C_{20}H_{19}N_3O_7S$: C, 53.93; H, 4.30; N, 9.43. Found: C, 54.12; H, 4.31; N, 9.44.

(2-9)

5-[[5-[(2-Diethylamino)ethoxy]-2-nitrophenyl]methylene]-2,4-imidazolidinedione

A mixture of 5-hydroxy-2-nitrobenzaldehyde (10 g, 60 mmol), 2-diethylaminoethyl chloride hydrochloride (13.4 g, 78 mmol), powdered potassium carbonate (24.8 g, 180 mmol) and dimethylformamide (200 mL) was heated at 100° C. in an oil bath. After 2 hours, the mixture was cooled, diluted with water and extracted with diethyl ether. The combined extracts were washed twice with wter, dried and the solvent evaporated to leave an oil (14.60 g, 92%) which was added, in one portion, to an ethanolic solution of the sodium salt of diethyl 2,4-dioxoimidazolidine-5-phosphonate [prepared by dissolving sodium (1.46 g, 0.06 g atom) in ethanol (200 mL) and adding diethyl 2,4-dioxoimidazolidine-5-phosphonate (13.00 g, 49 mmol)]. After 30 minutes, the mixture was diluted with water, filtered, the solid washed with water and dried in air to afford 5-[[5-[(2-diethylamino)ethoxy]2-nitrophenyl]methylene]-2,4-imidazolidinedione (11.0 g, 65%). An analytical sample was prepared by crystallization from aqueous dimethylformamide and had m.p. 208°–211° C. (dec).

Anal. Calcd. for $C_{16}H_{20}N_4O_5$: C, 55.17; H, 5.79; N, 16.09. Found: C, 55.12; H, 5.80; N, 15.98.

(2-10)

5-[[5-[[[3-(1-Methylethyl)-2-oxooxazolidin-5-yl]methyl]oxy]-2-nitrophenyl]methylene]-2,4-imidazolidinedione

Step 1

2-[2-Nitro-5-(oxiranylmethoxy)phenyl]1,3-dioxolane

A mixture of 2-(2-nitro-5-hydroxyphenyl)-1,3-dioxolane (29.5 g, 0.14 mole), epibromohydrin (29.03 g, 18.15 mL, 0.21 mole), potassium carbonate (48.67 g, 0.35 mole) and dimethylformamide (250 mL) was heated with stirring at 100° C. After 30 minutes, the mixture was cooled, diluted with wate and extracted with diethyl ether. The combined organic extracts were washed with water (3×), dried over sodium sulfate and concentrated to afford a crystalline solid (34.50 g, 92%) which was used without further purification. An analytical sample was prepared by dissolution of 1 g in dichloromethane (15 mL). Addition of hexane (about 50 mL), precipitated a yellow solid which was removed by filtration. Futher dilution with hexane precipitated 2-[2-nitro-5-(oxiranylmethoxy)phenyl]-1,3-dioxolane (0.8 g) m.p. 78°–79.5° C.

Anal. Calcd. for $C_{12}H_{13}NO_6$: C, 53.94; H, 4.91; N, 5.25. Found: C, 53.58; N, 4.82; H, 5.25.

Step 2

1-(1,3-dioxolan-2-yl)-4-nitrophenyl]3-[(1-methylethyl)amino]-2-propanol

A mixture of 2-[2-nitro-5-(oxiranylmethoxyoxy)phenyl]-1,3-dioxolane (2 g, 7.5 mmol) and isopropylamine (10 mL) was refluxed for 23 hours. The isopropylamine was removed in vacuo and the residue dissolved in dichloromethane, washed with water, dried and concentrated to afford a solid. Purification was effected by dissolving in dichloromethane and filtering through a plug of silica gel using 10% methanol/chloroform as eluant. The solid isolated was dissolved in dichloromethane and diluted with hexane to furnish 1-[3-(1,3-dioxolan-2-yl)-4-nitrophenyl]-3-[(1-methylethyl)amino]-2-propanol (0.8 g, 32%), m.p. 97°–99° C.

Anal. Calcd. for $C_{15}H_{22}N_2O_6$: C, 55.20; H, 6.80; N, 8.59. Found: C, 54.80; H, 6.69; N, 8.54.

Step 3

5-[[[3-(1-Methylethyl)-2-oxooxazolidin-5-yl]methyl]oxo]-2-nitrobenzaldehyde

Phosgene (11.12 g, 0.11 mole) in toluene (50 mL) was added dropwise to a stirred solution of 1-[3-(1,3-dioxolan-2-yl)-4-nitrophenyl]-3-[(1-methylethyl)amino]-2-propanol (14.65 g, 0.05 mole) and pyridine (8.88 g, 9.1 mL, 0.11 mole) in dichloromethane (150 mL) maintained at 0° C. in an ice bath. After completion of the addition, the ice bath was removed and the mixture warmed to room temperature and stirred for 15 minutes before being diluted with water. The mixture was extracted with dichloromethane, the combined extract dried and concentrated to afford an oil which was dissolved in tetrahydrofuran (300 mL). Dilute hydrochloric acid solution (75 mL) was added and the mixture heated to reflux. After 90 minutes, the tetrahydrofuran was evaporated and the residue extracted with dichloromethane. The combined extracts were dried over sodium sulfate and the solvent evaporated to leave an oil which crystallized to give a yellow solid (12.00 g, 86%). An analytical sample was prepared by dissolving a portion (1 g) in dichloromethane and adding diethyl ether to precipitate a tacky solid. After decanting, the solution was diluted with diethyl ether and then hexane to furnish 5-[[[3-(1-methylethyl)-2-oxooxazolidin-5-yl]methyl]oxy]-2-nitrobenzaldehyde (0.7 g, 74%), m.p. 94°–97° C.

Anal. Calcd. for $C_{14}H_{16}N_2O_6$: C, 54.54; H, 5.23; N, 9.09. Found: C, 54.26; H, 5.21; N, 9.04.

Step 4

5-[[5-[[[3-(1-Methylethyl)-2-oxooxazolidin-5-yl]methyl]oxy]-2-nitrophenyl]methylene]2,4-imidazolidinedione Sodium (0.9 g, 0.04 g atom) was dissolved in ethanol (150 mL) and diethyl 2,4-dioxoimidazolidine-5-phosphonate (9.19 g, 40 mmol) added. After 30 minutes solid 5-[[[3-(1-methylethyl)-2-oxooxazolidin-5-yl]methyl]oxy]-2-nitrobenzaldehyde (10.0 g, 32 mmol) was added and the mixture stirred vigorously. After 30 minutes, the mixture was diluted with water (150 mL) filtered and the solid washed with water and air dried to give 5-[[5-[[[3-(1-methylethyl)-2-oxooxazolidin-5-yl]methyl]oxy]-2-nitrophenyl]methylene]-2,4-imidazolidinedione (9.80 g, 77%). An analytical sample was prepared by crystallization from dimethylformamide and wate and had an m.p. 285°–287° C. (dec.).

Anal. Calcd. for $C_{17}H_{18}N_4O_7$: C, 52.31; H, 4.65; N, 14.35. Found: C, 51.84; H, 4.64; N, 14.25.

(2-11)

5-[[5-[[3-(1,1-Dimethylethyl)-2-oxooxazolidin-5-yl]-methoxy]-2-nitrophenyl]methylene]imidazolidine-2,4-dione Prepared from 5-[[[3-(1,1-dimethylethyl)-2-oxooxazolidin-5-yl]methyl]oxo]-2-nitrobenaldehyde and diethyl 2,4-dioxoimidazolidine-5-phosphonate analogous to the procedure of Example (2-10) (step 4), m.p. 273°–275° C. (dec).

Anal. Calcd. for $C_{18}H_{20}N_4O_7$: C, 53.46; H, 4.99; N, 13.86. Found: C, 53.35; H, 5.08; N, 13.86.

(2-12)

5-[[2-Nitro-5-[3-tetrahydro-2H-pyran-2-yl)oxy]propoxy]phenyl]methylene]-2,4-imidazolidinedione A mixture of 5-hydroxy-2-nitrobenzaldehyde (8.18 g, 49 mmol), 1-bromo-3-(tetrahydro-2H-pyran-2-yl)oxypropane (11.50 g, 51 mmol), potassium carbonate (7.16 g, 51 mmol), potassium iodide (catalytic amount) and dimethylformamide (800 mL) was heated with stirring at 110° C. for 30 minutes. The mixture was cooled, diluted with water (150 mL) and extracted with dichloromethane. The combined extracts were washed with water (3 times), dried over sodium sulfate and concentrated in vacuo to leave an oil which was dissolved in ethanol (15 mL) and added to a solution of sodium ethoxide (3.99 g, 58 mmol) and diethyl 2,4-dioxoimidazolidine-5-phosphonate (13.87 g, 58 mmol) in ethanol (200 mL). After 90 minutes, the ethanol was evaporated, the residue diluted with water and extracted with dichloromethane. The combined extracts were dried over sodium sulfate and concentrated in vacuo to afford an oil which was dissolved in dichloromethane and filtered through a plug of silica gel using diethyl ether as eluent. Evaporation of the solvent left 5-[[2-nitro-5-[3-tetrahydro-2H-pyran-2-yl)oxy]propoxy]phenyl]methylene-2,6-imidazolidinedione as a viscous oil which was used without further purification. An analytical sample of the 2,4-imidazolidine as a partial hydrate was prepared by precipitation from dichloromethane with hexane and had m.p. 128°–134° C.

Anal. Calcd. for $C_{18}H_{21}N_3O_7 \cdot 0.05H_2O$: C, 55.12; H, 5.43; N, 10.72; $H_2O$, 0.23. Found: C, 54.80; H, 5.33; N, 10.85; $H_2O$, 0.1

(2-13)

5-[[5-(2-Ethoxyethoxy)-2-nitrophenyl]methylene]-2,4-imidazolidinedione

A mixture of 5-hydroxy-2-nitrobenzaldehyde (1.00 g, 6 mmol), 2-bromoethyl ethyl ether (1.00 g, 0.74 mL, 6.5 mmol), powdered potassium carbonate (0.91 g, 6.5 mmol), potassium iodide (catalytic quantity) and dimethylformamide (10 mL) was heated with stirring at 110° C. After 30 minutes, the mixture was cooled, diluted with water and extracted with dichloromethane (3 times). Combined extracts were washed with water (2 times), dried over sodium thiosulfate and concentrated in vacuo to leave an oil which was dissolved in ethanol (3 mL) and added to a stirred solution of sodium ethoxide (0.53 g, 78 mmol) and diethyl 2,4-dioxoimidazolidine-5-phosphonate (1.83 g, 77 mmol) in ethanol (15 mL). After 10 minutes, the mixture was diluted with 2N hydrochloric acid solution and the solid filtered off and dried in air to give 5-[[5-(2-ethoxyethoxy)-2-nitrophenyl]methylene]-2,4-imidazolidinedione as a partial hydrate (1.40 g, 73%), m.p. 228°–233° C. (dec.).

Anal. Calcd. for $C_{14}H_{15}N_3O_6 \cdot 0.12H_2O$: C, 51.99; H, 4.75; N, 13.00; $H_2O$, 0.67. Found: C, 51.59; H, 4,72; N, 12.82; $H_2O$, 0.25. A second crop (0.2 g, 10%) was subsequently collected.

(2-14)

5-[[5-[3-(2-Methyl-1,3-dioxolan-2-yl)propoxy]-2-nitrophenyl]methylene]-2,4-imidazolidinedione A mixture of 5-hydroxy-2-nitrobenzaldehyde (20.00 g, 0.12 mole), 5-chloro-2-pentanone ethylene ketal (21.7 g, 0.132 mole), potassium carbonate (20.00 g, 0.14 mole), potassium iodide (0.5 g) and dimethylformamide (200 mL) was heated with stirring at 120° C. After 4 hours, the mixture was cooled, diluted with water and extracted with diethyl ether. The combined ethereal extracts were washed with water, dried over magnesium sulfate and the solvent evaporated. The residual oil comprised of 5-[3-(2-methyl-1,3-dioxolan-2-yl)propoxy]-2-nitrobenzaldehyde (used without purification) was dissolved in ethanol (200 mL) and added in one portion to a solution of sodium ethoxide (10.05 g, 0.15 mole) and diethyl 2,4-dioxoimidazolidine-5-phosphonate (35.00 g, 0.15 mole) in ethanol (300 mL). The mixture was stirred at room temperature for 90 minutes, concentrated to a volume of approximate 300 mL and diluted with water. The yellow precipitate was filtered off, washed with water and dried in vacuo at 70° C. to give 5-[[5-[3-(2-methyl-1,3dioxolan-2-yl)propoxy]-2-nitrophenyl]methylene]-2,4-imidazolidinedione (38.01 g, 84%). An analytical sample was prepared by crystallization from ethanol and had m.p. 175°–180° C.

Anal. Calcd. for $C_{17}H_{19}N_3O_7$: C, 54.11; H, 5.08; N, 11.14. Found: C, 54.34; H, 50.8; N, 10.85.

(2-15)

5-[[2-Nitro-5-[3-(Phenylsulfonyl)propoxy]phenyl]methylene]-2,4-imidazolidinedione Prepared from 2-nitro-5-[3-(phenylsulfonyl)propoxy]benzaldehyde (obtained by alkylating 5-hydroxy-2-nitrobenzaldehyde with 3-phenylsulfonylpropyl bromide) and diethyl 2,4-dioxoimidazolidine-5-phosphonate analogous to the procedure of Example (2-8), m.p. 125°–157° C.

Anal. Calcd. for $C_{19}H_{17}N_3O_7S$: C, 52.90; H, 3.97; N, 9.74. Found: C, 52.81; H, 4.10; N, 9.71.

(2-16)

1-Methyl-5-[[2-nitro-5-[3-(phenylsulfonyl)propoxy]phenyl]methylene]-2,4-imidazolidinedione Prepared from 2-nitro-5-[3-(phenylsulfonyl)propoxy]benzaldehyde and diethyl 1-methyl-2,4-dioxoimidazolidine-5-phosphonate analogous to the procedure of Example (2-8), m.p. 147°–158° C.

Anal. Calcd. for $C_{20}H_{19}N_3O_7S$: C, 53.93; H, 4.30; N, 9.43. Found: C, 54.07; H, 4.50; N, 9.21.

(2-17)

2-[3-[(2,4-Dioxoimidazolidin-5-ylidene)methyl]-4-nitrophenoxy]ethyl Acetate

Diethyl 2,4-dioxoimidazolidine-5-phosphonate was added to triethylamine (equimolar) in acetonitrile. After one hour, an equimolar amount of 4-[3-formyl-4-nitrophenoxy]ethyl acetate (obtained by alkylating 5-hydroxy-2-nitrobenzaldehyde with 2-bromoethyl acetate) was added and the mixture stirred for 2 hours. Isolation of the product according to the procedure of Example (2-1) provided 2-[3-[(2,4-dioxoimidazolidin-5-ylidene)methyl]-4-nitrophenoxy]ethyl acetate, m.p. indistinct.

Anal. Calcd. for $C_{14}H_{13}N_{13LI}N_3O_7$: C, 50.16; H, 3.91; N, 12.54. Found: C, 49.90; H, 3.98; N, 12.68.

(2-18)

3-[3-[(2,4-Dioxoimidazolidin-5-ylidene)methyl]-4-nitrophenoxy]propyl Acetate

Prepared from diethyl 2,4-dioxoimidazolidine-5-phosphonate and ethyl 4-[3-formyl-4-nitrophenoxy]propyl acetate (obtained by alkylating 5-hydroxy-2-nitrobenzaldehyde with 3-bromopropyl acetate) analogous to the procedure of Example (2-17), m.p. 94°–130° C.

Anal. Calcd. $C_{15}H_{15}N_3O_7$: C, 51.58; H, 4.33; N, 12.03. Found: C, 51.56; H, 4.36; N, 12.27.

EXAMPLE 3

Additional hydantoin intermediates of Formula II illustrated below may be prepared by following the procedures of Example 2 (Method B) employing appropriate 2-nitrobenzaldehydes and hydantoin-5-phosphonates.

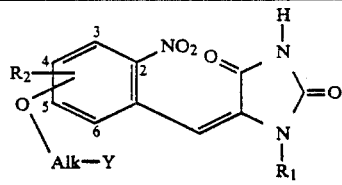

(II)

| | | R₂ | | O—Alk—Y | |
|---|---|---|---|---|---|
| Entry | R₁ | Position | Radical | Position | Radical |
| 3-1 | H | 6 | Cl | 5 | O(CH₂)₃CO₂Et |
| 3-2 | H | 3 | Cl | 5 | O(CH₂)₃CO₂Et |
| 3-3 | H | 4 | Cl | 5 | O(CH₂)₃CO₂Et |
| 3-4 | H | 3 | F | 5 | O(CH₂)₃CO₂Et |
| 3-5 | H | 6 | F | 5 | O(CH₂)₃CO₂Et |
| 3-6 | H | 6 | Me | 5 | O(CH₂)₃CO₂Et |
| 3-7 | H | 5 | F | 6 | O(CH₂)₃CO₂Et |
| 3-8 | H | 3 | Cl | 6 | O(CH₂)₃CO₂Et |
| 3-9 | H | 4 | F | 6 | O(CH₂)₃CO₂Et |
| 3-10 | H | — | H | 6 | O(CH₂)₃CO₂Et |
| 3-11 | H | 4 | Me | 6 | O(CH₂)₃CO₂Et |
| 3-12 | H | 5 | F | 6 | O(CH₂)₃CO₂Et |
| 3-13 | H | — | H | 3 | O(CH₂)₃CO₂Et |
| 3-14 | H | 5 | Me | 3 | O(CH₂)₃CO₂Et |
| 3-15 | H | 5 | F | 4 | O(CH₂)₃CO₂Et |
| 3-16 | H | 5 | Cl | 4 | O(CH₂)₃CO₂Et |
| 3-17 | H | — | H | 4 | O(CH₂)₃CO₂Et |
| 3-18 | H | 6 | Me | 4 | O(CH₂)₃CO₂Et |
| 3-19 | H | 4 | F | 3 | O(CH₂)₃CO₂Et |
| 3-20 | H | 4 | Cl | 3 | O(CH₂)₃CO₂Et |
| 3-21 | H | — | H | 5 | O(CH₂)₆CO₂Et |
| 3-22 | H | 6 | Cl | 5 | O(CH₂)₆CO₂Et |
| 3-23 | H | 6 | Me | 5 | O(CH₂)₆CO₂Et |
| 3-24 | H | 3 | Cl | 5 | O(CH₂)₆CO₂Et |
| 3-25 | H | — | H | 6 | O(CH₂)₆CO₂Et |
| 3-26 | H | 3 | F | 6 | O(CH₂)₆CO₂Et |
| 3-27 | H | 4 | Me | 6 | O(CH₂)₆CO₂Et |
| 3-28 | H | 4 | Cl | 6 | O(CH₂)₆CO₂Et |
| 3-29 | H | — | H | 3 | O(CH₂)₆CO₂Et |
| 3-30 | H | 6 | F | 3 | O(CH₂)₆CO₂Et |
| 3-31 | H | 4 | Cl | 3 | O(CH₂)₆CO₂Et |
| 3-32 | H | 5 | Me | 3 | O(CH₂)₆CO₂Et |
| 3-33 | H | — | H | 4 | O(CH₂)₆CO₂Et |
| 3-34 | H | 6 | Me | 4 | O(CH₂)₆CO₂Et |
| 3-35 | H | — | H | 6 | O(CH₂)₄CO₂Et |
| 3-36 | H | 3 | Cl | 6 | O(CH₂)₄CO₂Et |
| 3-37 | H | 3 | Me | 6 | O(CH₂)₄CO₂Et |
| 3-38 | H | 5 | Me | 6 | O(CH₂)₄CO₂Et |
| 3-39 | H | 3 | Cl | 5 | O(CH₂)₄CO₂Et |
| 3-40 | H | 6 | Cl | 5 | O(CH₂)₄CO₂Et |
| 3-41 | H | — | H | 5 | O(CH₂)₄CO₂Et |
| 3-42 | H | — | H | 4 | O(CH₂)₄CO₂Et |
| 3-43 | H | 6 | Me | 4 | O(CH₂)₄CO₂Et |
| 3-44 | H | 5 | Cl | 4 | O(CH₂)₄CO₂Et |
| 3-45 | H | 4 | Cl | 5 | O(CH₂)₄CO₂Et |
| 3-46 | H | — | H | 3 | O(CH₂)₄CO₂Et |
| 3-47 | H | 6 | Me | 3 | O(CH₂)₄CO₂Et |
| 3-48 | H | 4 | Cl | 3 | O(CH₂)₄CO₂Et |
| 3-49 | H | — | H | 6 | O(CH₂)₅CO₂Et |
| 3-50 | H | 3 | Cl | 6 | O(CH₂)₅CO₂Et |
| 3-51 | H | 5 | Cl | 6 | O(CH₂)₅CO₂Et |
| 3-52 | H | — | H | 5 | O(CH₂)₅CO₂Et |
| 3-53 | H | 4 | Cl | 5 | O(CH₂)₅CO₂Et |
| 3-54 | H | 3 | Me | 5 | O(CH₂)₅CO₂Et |
| 3-55 | H | — | H | 3 | O(CH₂)₅CO₂Et |
| 3-56 | H | 4 | F | 3 | O(CH₂)₅CO₂Et |
| 3-57 | H | 5 | Me | 3 | O(CH₂)₅CO₂Et |
| 3-58 | H | — | H | 4 | O(CH₂)₅CO₂Et |
| 3-59 | H | 5 | Me | 4 | O(CH₂)₅CO₂Et |
| 3-60 | H | 6 | Cl | 4 | O(CH₂)₅CO₂Et |
| 3-61 | H | 6 | Cl | 5 | OCH₂CO₂Et |
| 3-62 | H | — | H | 5 | OCH₂CO₂Et |
| 3-63 | H | 3 | Cl | 5 | OCH₂CO₂Et |
| 3-64 | H | 4 | Cl | 5 | OCH₂CO₂Et |
| 3-65 | H | 3 | F | 5 | OCH₂CO₂Et |
| 3-66 | H | — | H | 5 | O(CH₂)₂CO₂Et |
| 3-67 | H | 4 | Cl | 5 | O(CH₂)₂CO₂Et |
| 3-68 | CH₃ | — | H | 5 | OCH₂CO₂Et |
| 3-69 | CH₃ | — | H | 5 | O(CH₂)₂CO₂Et |
| 3-70 | CH₃ | — | H | 5 | O(CH₂)₅CO₂Et |

-continued

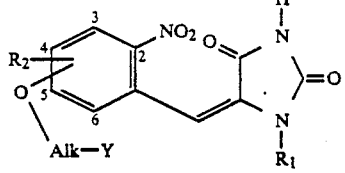
(II)

| Entry | R₁ | R₂ Position | R₂ Radical | O—Alk—Y Position | O—Alk—Y Radical |
|---|---|---|---|---|---|
| 3-71 | CH₃ | — | H | 5 | O(CH₂)₆CO₂Et |
| 3-72 | CH₃ | — | H | 6 | O(CH₂)₃CO₂Et |
| 3-73 | CH₃ | — | H | 3 | O(CH₂)₃CO₂Et |
| 3-74 | CH₃ | — | H | 4 | O(CH₂)₃CO₂Et |
| 3-75 | (CH₃)₂CH | — | H | 5 | O(CH₂)₃CO₂Et |
| 3-76 | C₆H₅CH₂ | — | H | 5 | O(CH₂)₃CO₂Et |
| 3-77 | H | 6 | OMe | 5 | O(CH₂)₃CO₂Et |
| 3-78 | H | 3 | OMe | 5 | O(CH₂)₃CO₂Et |
| 3-79 | H | 4 | OMe | 5 | O(CH₂)₃CO₂Et |
| 3-80 | H | 4 | OCH(CH₃)₂ | 5 | O(CH₂)₃CO₂Et |
| 3-81 | H | — | H | 5 | 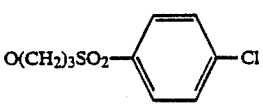 |

EXAMPLE 4

4-[(2,3-Dihydro-2-oxo-1$\underline{H}$-imidazo[4,5-b]quinolin-7-yl)oxy]butanoic Acid

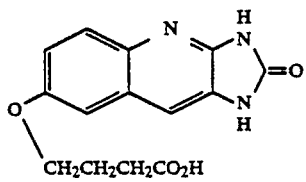

A solution of ethyl 4-[3-[(2,4-dioxoimidazolidin-5-ylidene]methyl]-4-nitrophenoxy]butanoate (40.0 g, 0.11 mol) in dimethylformamide (300 mL) was hydrogenated over 10% palladium on charcoal (4.0 g) at 55 p.s.i. After 42 hours, the mixture was filtered through kieselguhr, the solvent evaporated and methanol (500 mL) added. The mixture was heated to reflux and iodine (27.9 g, 0.11 mol) added portionwise. The mixture was refluxed for 45 minutes, cooled and diluted with 10% sodium thiosulfate solution and 10% sodium carbonate solution to pH=7. The mixture was concentrated to about 250 mL in vacuo and filtered to afford a grey solid (31.6 g) which was suspended in a mixture of methanol (500 mL) and water (250 mL). Sodium hydroxide solution (4N, 72 mL) was added and the mixture stirred at room temperature for 16 hours and partially evaporated. Acidification with 6N hydrochloric acid solution (to pH=2) precipitated 4-[(2,3-dihydro-2-oxo-1$\underline{H}$-imidazo[4,5-b]quinolin-7-yl)oxy]butyric acid (26.2 g 83%). An analytical sample was prepared by crystallization from aqueous dimethylformamide and had m.p. 321°-323° C. (dec.).

Anal. Calcd. for C₁₄H₁₃N₃O₄: C, 58.53; H, 4.56; N, 14.63. Found: C, 58.43; H, 4.62; N, 14.69.

NMR (DMSO-d₆) delta 2.08 (2H, m, OCH₂CH₂), 2.51 (2H, m. CH₂CO₂H), 4.11 (2H, m, OCH₂), 7.21 (1H, dd, J=9 Hz, J'=2 Hz, aromatic $\underline{H}$ ortho to —O—), 7.36 (1H, d, J=2 Hz, aromatic $\underline{H}$ ortho to —O—), 7.59 (1H, s, aromatic $\underline{H}$ ortho to N$\underline{H}$.CO), 7.77 (1H, d, J=9 Hz, aromatic $\underline{H}$ meta to —O—), 11.05 (1H, bs, N$\underline{H}$) and 11.84 (2H, bs, N$\underline{H}$+COO$\underline{H}$).

EXAMPLE 5

4-[(2,3-Dihydro-2-oxo-1$\underline{H}$-imidazo[4,5-b]quinolin-7-yl)oxy]butanoic Acid

Methyl 4-[(2,3-dihydro-2-oxo-1$\underline{H}$-b]quinolin-7-yl)oxy]butanoate (1.0 g, 3.3 mmol) was added to a solution of 50% aqueous methanol containing 4N NaOH (2 mL). After stirring for 1 hour, the mixture was acidified to pH=3 by the addition of 2N HCl. The precipitate was washed with water, methanol and diethyl ether to give 4-[(2,3-dihydro-2-oxo-1$\underline{H}$-imidazo[4,5-b]quinolin-7-yl)oxy]butyric acid as a partial hydrate (0.84 g, 88%). An analytical sample was prepared by crystalization from dimethylformamide/H₂O and had m.p.>320°.

Anal. Calcd. for C₁₄H₁₃N₃O₄ 0.1H₂O: C, 58.17; H, 4.60; N, 14.54; H₂O, 0.62. Found: C, 57.87; H, 4.90; N, 14.47; H₂O, 0.63.

NMR (DMSO-d₆): delta 2.15 (2H, m, OCH₂CH₂), 2.49 (2H, t, J=7 Hz, CH₂CO₂H), 4.11 (2H, t, J=6 Hz, OCH₂), 7.19 (1H, dd, J=9 Hz, J'=2 Hz, aromatic $\underline{H}$ ortho to —O—), 7.36 (1H, d, J=2 Hz, aromatic $\underline{H}$ ortho to —O—), 7.55 (1H, s, aromatic $\underline{H}$ ortho to N$\underline{H}$.CO), 7.75 (1H, d, J=9 Hz, aromatic $\underline{H}$ meta to —O—), 10.96 (1H, bs, N$\underline{H}$), and 11.60 (2H, bs, N$\underline{H}$+CO₂$\underline{H}$).

EXAMPLE 6

4-[(2,3-Dihydro-1-methyl-2-oxo-1H-imidazo[4,5-b]quinolin-7-yl)oxy]butanoic Acid

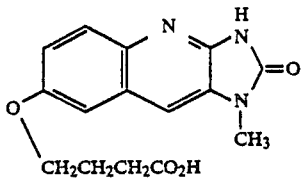

This compound was prepared from ethyl 4-[3-[(1-methyl-2,4-dioxoimidazolidin-5-ylidene)methyl]-4-nitrophenoxy]butanoate analogous to Example 4, m.p. 286°-288.5° C.

Anal. Calcd. for $C_{15}H_{15}N_3O_4$: C, 59.80; H, 5.02; N, 13.95. Found: C, 59.70; H, 5.11; N, 13.77.

NMR (DMSO-d$_6$): delta 2.00 to 2.04 (2H, m, —C$\underline{H}_2$—), 2.45 (2H, t, J=7 Hz, C$\underline{H}_2$CO$_2$H), 3.34 (3H, s, N—C$\underline{H}_3$), 4.08 (2H, t, J=6 Hz, O—C$\underline{H}_2$), 7.18 (1H, dd, J=9 $\underline{H}$z, J'=2 Hz, aromatic $\underline{H}$ ortho to —O—), 7.28 (1H, d, J=2 Hz, aromatic $\underline{H}$ ortho to —O—), 7.62 (1H, s, aromatic $\underline{H}$ ortho to —N$\underline{H}$CO), 7.72 (1H, d, J=9 Hz, aromatic $\underline{H}$ meta to —O—), 11.00 to 12.20 (2H, bs, N$\underline{H}$CO and CO$_2\underline{H}$.

EXAMPLE 7

2-[(1,3-Dihydro-2-oxo-2H-imidazo[4,5-b]quinolin-7-yl)oxy]acetic Acid

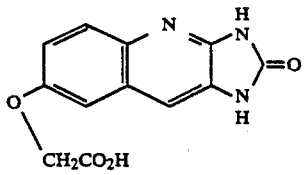

This compound was prepared from ethyl [3-[(2,4-dioxoimidazolidin-5-ylidene)methyl]-4-nitrophenoxy]acetate analogous to Example 4, obtained as a partial hydrate, m.p. 340°-342° C. (dec.).

Anal. Calcd. for $C_{12}H_9N_3O_4 \cdot 0.15H_2O$: C, 55.03; H, 3.58; N, 16.05; H$_2$O, 1.03. Found: C, 54.65; H, 3.79; N, 15.91; H$_2$O, 0.67.

NMR (DMSO-d$_6$/CF$_3$CO$_2$H): delta 4.34 (2H, s, C$\underline{H}_2$CO$_2$H), 7.14 (2H, m, aromatic $\underline{H}$ ortho to —O—), 7.43 (1H, aromatic $\underline{H}$ ortho to —N$\underline{H}$CO—), 7.64 (1H, d, J=9 Hz, aromatic $\underline{H}$ meta to —O—).

EXAMPLE 8

5-[(2,3-Dihydro-2-oxo-1H-imidazo[4,5-b]quinolin-7-yl)oxy]pentanoic Acid

This compound was prepared from 5-[[4-nitro-3-[(2,4-dioxoimidazolidin-5-ylidene)methyl]pentyl]oxy]-pentanoic acid or ethyl 5-[3-[(2,4-dioxoimidazolidin-5-ylidene)methyl]-4-nitrophenoxy]pentanoate analogous to Example 4, m.p. 317°-318° C.

Anal. Calcd. for $C_{15}H_{15}N_3O_4$: C, 59.80; H, 5.02; N, 13.95. Found: C, 59.46; H, 5.34; N, 13.95.

NMR (DMSO-d$_6$): delta 1.70 to 1.90 (4H, m, OCHCH$_2$CH$_2$—), 2.39 (2H, m, C$\underline{H}_2$CO$_2$H), 4.08 (2H, bs, —OC$\underline{H}_2$—), 7.21 (1H, d, J=9 Hz, aromatic $\underline{H}$ ortho to —O—), 7.34 (1H, s, aromatic $\underline{H}$ ortho to —O—), 7.60 (1H, s, aromatic $\underline{H}$ ortho to —NH.CO), 7.78 (1H, d, J=9 Hz, aromatic $\underline{H}$ meta to —O—), 11.06 (1H, s, N$\underline{H}$.CO) and 11.50-12.10 (1H, bs, CO$_2\underline{H}$).

EXAMPLE 9

5-[(2,3-Dihydro-1-methyl-2-oxo-1H-imidazo[4,5-b]quinolin-7-yl)oxy]pentanoic Acid

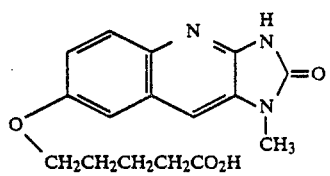

This compound was prepared from ethyl 5-[3-[(1-methyl-2,4-dioxoimidazolidin-5-ylidene)methyl]-4-nitrophenoxy]pentanoate analogous to Example 4, m.p. 311°-313° C.

Anal. Calcd. for $C_{16}H_{17}N_3O_4$: C, 60.95; H, 5.43; N, 13.33. Found: C, 60.72; H, 5.42; N, 13.20.

NMR (DMSO-d$_6$): delta 1.69-1.80 (4H, m, OCH$_2$CH$_2$CH$_2$), 2.31 (1H, t, J=7 Hz), CH$_2$CO$_2$H), 3.34 (3H, s, $\overline{\text{NCH}_3}$), 4.08 (2H, t, J=6 Hz, OC$\underline{H}_2$), 7.17 (1H, dd, J=9 $\underline{H}$z, J'=2.5 Hz, aromatic $\underline{H}$ ortho to —O—), 7.30 (1H, d, J=2.5 Hz, aromatic $\overline{H}$ ortho to —O—), 7.64 (1H, s, aromatic $\underline{H}$ ortho to N$\overline{H}$.CO), 7.71 (1H, d, J=9 Hz, aromatic $\underline{H}$ meta to —O—).

EXAMPLE 10

Methyl 4-[(2,3-Dihydro-2-oxo-1H-imidazo[4,5-b]quinolin-7-yl)oxy]butanoate

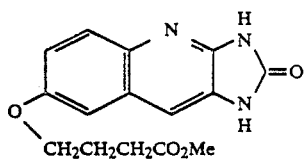

A solution of 4-[3-(2,4-dioxoimidazolidin-5-ylidene)-methyl]-4-nitrophenoxy]butanoic acid (12.75 g, 38 mmol) in dimethylformamide (85 mL) was hydrogenated over 10% palladium on charcoal (1.28 g) at 60 p.s.i. in a low pressure hydrogenation apparatus. After 28 hours, the mixture was filtered through kieselguhr, the solvent evaporated and the residue diluted with methanol (250 mL). The mixture was heated to reflux, iodine (9.64 g, 38 mmol) added portionwise and reflux continued for 30 minutes. The mixture was concentrated to about 250 mL and diluted with 10% sodium thiosulfate solution and 10% sodium carbonate solution until pH=7. The precipitate was filtered off, washed with water and methanol and dried in air to afford methyl 4-[(2,3-dihydro-2-oxo-1H-imidazo[4,5-b]quinolin-7-yl)oxy]butanoate (8.77 g, 77%). An analytical sample was prepared by crystallizing twice from aqueous dimethylformamide and had m.p. 299°-301° C.

Anal. Calcd. for C₁₅H₁₅N₃O₄: C, 59.80; H, 5.02; N, 13.95. Found: C, 59.62; H, 5.00; N, 13.90.

NMR (DMSO-d₆): delta 2.05 (2H, m, OCH₂C$\underline{H}$₂), 2.53 (2H, t, J=7 Hz CH₂CO₂CH₃), 3.63 (3H, s, CO₂CH₃), 4.08 (2H, t, J=6 Hz, OC$\underline{H}$₂), 7.15 (1H, dd, J=9 Hz, J'=2.5 Hz, aromatic $\underline{H}$ ortho to —O—), 7.33 (1H, d, J=2.5 Hz, aromatic $\underline{H}$ ortho to —O—), 7.53 (1H, s, aromatic $\underline{H}$ ortho to N$\underline{H}$.CO), 7.70 (1H, d, J=9 Hz, aromatic $\underline{H}$ meta to —O—), 10.97 (1H, s, N$\underline{H}$) and 11.38 (1H, s, N$\underline{H}$).

EXAMPLE 11

Methyl 4-[(2,3-Dihydro-1-methyl-2-oxo-1$\underline{H}$-imidazo[4,5-b]quinolin-7-yl)oxy]butanoate

This compound was prepared from ethyl 4-[3-[(1-methyl-2,4-dioxoimidazolidin-5-ylidine)methyl]-4-nitrophenoxy]butanoate analogous to Example 10, m.p. 222–224° C.

Anal. Calcd. for C₁₆H₁₇N₃O₄: C, 60.95; H, 5.43; N, 13.33. Found: C, 61.14; H, 5.46; N, 13.41.

NMR (DMSO-d₆): delta 2.05 (1H, q, J=7 Hz, —OCH₂C$\underline{H}$₂), 2.53 (2H, 5, J=7H, —C$\underline{H}$₂CO₂CH₂), 3.34 (3H, s, NCH₃), 3.63 (3H, s, —CO₂C$\underline{H}$₃), 4.08 (2H, t, J=7 Hz, —OC$\underline{H}$₃), 7.16 (1H, dd, J=9 Hz, J'=2.7 Hz, aromatic $\underline{H}$ ortho to —O—), 7.28 (1H, d, J=2.7 Hz, aromatic $\underline{H}$ ortho to —O—), 7.63 (1H, s, aromatic $\underline{H}$ ortho to N$\underline{H}$.CO), 7.71 (1H, d, J=9 Hz, aromatic $\underline{H}$ meta to —O—), and 11.58 (1H, s, N$\underline{H}$).

EXAMPLE 12

Ethyl [(2,3-Dihydro-2-oxo-1$\underline{H}$-imidazo[4,5-b]quinolin-7-yl)oxy]acetate

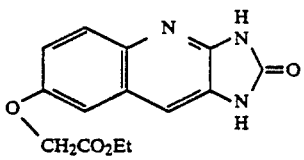

This compound was prepared from ethyl [3-[(2,4-dioxoimidazolidin-5-ylidene)methyl]-4-nitrophenoxy]acetate analogous to Example 10. The material obtained from the iodine treatment was taken up in ethanol saturated with hydrogen chloride. After standing for 2–12 hours, the mixture was concentrated and crystallized from ethanol/ether to provide as a partially hydrated hydrochloride salt the title compound, m.p. 304°–306° C.

Anal. Calcd. for C₁₄H₁₃N₃O₄.HCl.0.3H₂O: C, 51.09; H, 4.48; N, 12.77; H₂O, 1.64. Found: C, 51.29; H, 4.52; N, 12.81; H₂O, 1.89.

NMR (DMSO-d₆): delta 1.24 (3H, t, J=7 Hz, OCH₂C$\underline{H}$₃), 4.11 (2H, q, J=7 Hz, O.C$\underline{H}$₂.CH₃), 4.89 (2H, s, O.C$\underline{H}$₂.CO₂Et), 7.32 (1H, dd, J=9 Hz, J'=2.7 Hz, aromatic $\underline{H}$ ortho to —O—CH₂), 7.47 (1H, d, J=2.7 Hz, aromatic $\underline{H}$ ortho to —O—CH₂), 7.77 (1H, s, aromatic $\underline{H}$ ortho to —NH.CO), and 7.93 (1H, d, J=9 Hz, aromatic $\underline{H}$ meta to —O—CH₂—).

EXAMPLE 13

Methyl 5-[(2,3-Dihydro-2-oxo-1$\underline{H}$-imidazo[4,5-b]quinolin-7-yl)oxy]pentanoate

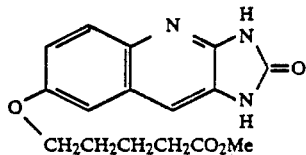

This compound was prepared from ethyl 5-[3-[(2,4-dioxoimidazolidin-5-ylidene)methyl]-4-nitrophenoxy]-pentanoate analogous to Example 11, m.p. 281°–282° C.

Anal. Calcd. for C₁₆H₁₇N₃O₄: C, 60.94; H, 5.43; N, 13.33. Found: C, 60.90; H, 5.48; N, 13.28.

NMR (DMSO-d₆): delta 1.73 to 1.79 (4H, m, —O—CH₂.C$\underline{H}$₂.C$\underline{H}$₂), 2.41 (2H, t, J=7 Hz, C$\underline{H}$₂.CO₂CH₃), 3.61 (3H, s, CO₂C$\underline{H}$₃), 4.06 (2H, t, J=6 Hz, —O—C$\underline{H}$₂), 7.16 (1H, dd, J=9 Hz, J'=2.6 Hz, aromatic $\underline{H}$ ortho to —O—), 7.33 (1H, d, J=2.6 Hz, aromatic $\underline{H}$ ortho to —O—), 7.53 (1H, s, aromatic $\underline{H}$ ortho to NH.CO), 7.70 (1H, d, J=9 Hz, aromatic $\underline{H}$ meta to —O—), 10.98 (1H, s, N$\underline{H}$CO), and 11.40 (1H, s, N$\underline{H}$.CO).

EXAMPLE 14

Methyl 5-[(2,3-Dihydro-1-methyl-2-oxo 1$\underline{H}$-imidazo[4,5-b]quinolin-7-yl)oxy]pentanoate

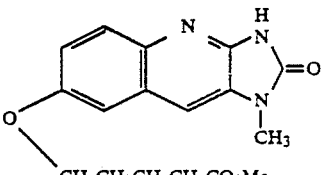

This compound was prepared from ethyl 5-[3-[(1-methyl-2,4-dioxoimidazolidin-5-ylidene)methyl]-4-nitrophenoxy]pentanoate analogous to Example 11, m.p. 223°–225° C.

Anal. Calcd. for C₁₇H₁₉N₃O₄: C, 62.00; H, 5.82; N, 12.76. Found: C, 61.97; H, 5.87; N, 13.08.

NMR (DMSO-d₆): delta 1.73 to 1.79 (4H, m, —O—CH₂CH₂C$\underline{H}$₂), 2.41 (2H, t, J=7 Hz, C$\underline{H}$₂.CO₂CH₃), 3.34 (3H, s, NCH₃), 3.60 (3H, s, CO₂CH₃), 4.06 (2H, t, J=6 Hz, —O—C$\underline{H}$₂), 7.17 (1H, dd, J=9 Hz, J'=2.5 Hz, aromatic $\overline{H}$ ortho to —O—), 7.29 (1H, d, J=2.5 Hz), aromatic $\underline{H}$ ortho to —O—), 7.63 (1H, s, aromatic $\underline{H}$ ortho to NH.CO), 7.71 (1H, d, J=9.1 Hz, aromatic $\underline{H}$ meta to —O—), and 11.57 (1H, s, N$\underline{H}$.CO).

EXAMPLE 15

4-[4-[(2,3-Dihydro-2-oxo-1H-imidazo[4,5-b]quinolin-7-oxy]-1-oxobutyl]morpholine

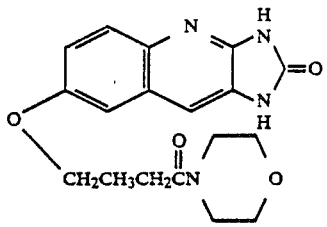

A stirred mixture of 4-[(2,3-dihydro-2-oxo-1H-imidazo[4,5-b]quinolin-7-yl)oxy]butyric acid (2.01 g, 7 mmol), morpholine (0.68 g, 7.8 mmol) and dimethylformamide (60 mL) was cooled to −20° C. and triethylamine (1.53 g, 2.1 mL, 15 mmol) and diphenylphosphoryl azide (2.15 g, 1.68 mL, 7.8 mmol) added. The mixture was maintained at −20° C. for 2 hours, warmed to room temperature and stirred overnight. Dichloromethane (200 mL) was added and the mixture was filtered to give 4-[4-[(2,3-dihydro-2-oxo-1H-imidazo[4,5-b]quinolin-7-yl)oxo]-1-oxobutyl]morpholine (2.08 g, 84%). An analytical sample was prepared by crystallizing from aqueous dimethylformamide and had m.p. 274°–276° C.

Anal. Calcd. for $C_{18}H_{20}N_4O_4$: C, 60.67; H, 5.66; N, 15.72. Found: C, 60.73; H, 5.70; N, 16.03.

NMR (DMSO-$d_6$): delta 2.03 (2H, m, OCH$_2$CH$_2$), 2.52 (2H, m, CH$_2$CO), 3.47 (4H, bs, morpholino H), 3.56 (4H, bs, morpholino H), 4.09 (2H, m, OCH$_2$), 7.17 (1H, dd, J=9 Hz, J'=2 Hz, aromatic H ortho to —O—), 7.34 (1H, d, J=2 Hz, aromatic H ortho to —O—), 7.54 (1H, s, aromatic H ortho to NH.CO), 7.71 (1H, d, J=9 Hz, aromatic H meta to —O—), 11.00 (1H, s, NH), and 11.42 (1H, s, NH).

EXAMPLE 16

4-[(2,3-Dihydro-2-oxo-1H-imidazo[4,5-b]quinolin-7-yl)oxy]-N-(tricyclo[3.3.1$^{3,7}$]decan-7-yl)butanamide

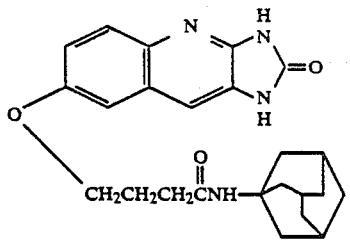

A stirred mixture of 4-[(2,3-dihydro-2-oxo-1H-imidazo[4,5-b]quinolin-7-yl)oxy]butyric acid (2,87 g, 10 mmol), adamantanamine (1.87 g, 12 mmol), dimethylformamide (250 mL) and tetrahydrofuran (65 mL) was cooled to −20° C. Triethylamine (2.12 g, 2.9 mL, 21 mmol) and diphenylphosphoryl azide (4.16 g, 2.6 mL, 12 mmol) were added, the mixture stirred at −20° C. for 2 hours and then warmed to room temperature. After 18 hours, the tetrahydrofuran was evaporated in vacuo, the residue diluted with dichloromethane (200 mL), washed with dilute sodium carbonate solution and water. The organic phase was dried over sodium sulphate and the solvent removed to give a solid which was suspended in methanol and filtered to give partially hydrated 4-[(2,3-dihydro-2-oxo-1H-imidazo[4,5-b]quinolin-7-yl)oxy]-N-(tricyclo[3.3.1$^{3,7}$]decan-7-yl)butanamide (2.65 g, 63%), m.p. 304°–306° C.

Anal. Calcd. for $C_{24}H_{28}N_4O_3$: C, 68.55; H, 6.71; N, 13.32. Found: C, 68.34; H, 6.64; N, 13.30.

NMR (DMSO-$d_6$): delta 1.61 (11H, s, adamantyl H), 1.95–2.05 (6H, m, adamantyl H+CH$_2$CH$_2$O), 2.28 (2H, m, CH$_2$.CO), 4.06 (2H, t, J=6 Hz, —OCH$_2$—), 7.18 (1H, d, J=9 Hz aromatic H ortho to —O—), 7.33 (2H, s, aromatic H ortho to —O—+NH), 7.54 (1H, s, aromatic H ortho to NH.CO), 7.72 (1H, d, J=9 Hz, aromatic H meta to —O—), and 11.19 (2H, bs, NH).

EXAMPLE 17

N-Cyclopentyl-4-[(2,3-dihydro-2-oxo-1H-imidazo[4,5-b]quinolin-7-yl)oxy]butanamide

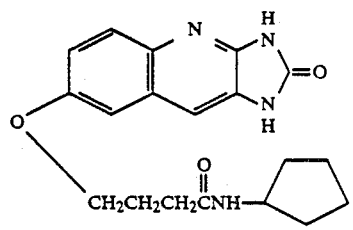

This compound, m.p. >320° C., was prepared analogous to Example 15 from 4-[(2,3-dihydro-2-oxo-1H-imidazo[4,5-b]quinolin-7-yl)oxy]butyric and cyclopentylamine.

Anal. Calcd. for $C_{19}H_{22}N_4O_3$: C, 64.39; H, 6.26; N, 15.81. Found: C, 64.01; H, 6.18; N, 15.73.

NMR (DMSO-$d_6$): delta 1.45 (2H, m, CH$_2$), 1.48 (2H, m, CH$_2$), 1.59 (2H, m, CH$_2$), 1.78 (2H, m, CH$_2$), 2.00 (2H, m, —O—CH$_2$.CH$_2$), 2.27 (2H, t, J=7 Hz, —CH$_2$.CONH—), 3,98 to 4.07 (3H, m, O—CH$_2$ and N—CH), 7.15 (1H, dd, J=9 Hz, J'=2.5 Hz, aromatic H ortho to —O—), 7.32 (1H, d, J=2.5 Hz, aromatic H ortho to —O—), 7.52 (1H, s, aromatic H ortho to NH.CO), 7.69 (1H, d, J=9 Hz, aromatic H meta to —O—), 7.82 (1H, d, J=7 Hz, CO.NH—cyclopentyl), 10.97 (1H, s, NHCO) and 11.37 (1H, s, NH.CO).

EXAMPLE 18

N-Cyclohexyl-4-[(2,3-dihydro-2-oxo-1H-imidazo[4,5-b]quinolin-7-yl)oxy]butanamide

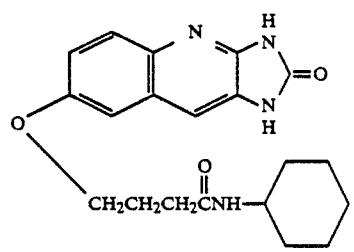

This compound, m.p. >320° C., was prepared analogous to Example 15 from 4-[(2,3-dihydro-2-oxo-1H-imidazo[4,5-b]quinolin-7-yl)oxy]butyric acid and cyclohexylamine.

Anal. Calcd. for C, $_{20}H_{24}N_4O_3$: C, 65.20; H, 6.57; N, 15.21. Found: C, 65.19; H, 6.68; N, 15.38.

NMR (DMSO-$D_6$): delta 1.00 to 1.80 (10H, m, CH$_2$), 1.99 (2H, m, —O—CH$_2$.CH$_2$), 2.27 (2H, t, J=7 Hz, CH$_2$.CO.NH), 3.55 (1H, m, CO.NH.CH), 4.04 (2H, t, J=6 Hz, —O—CH₂), 7.15 (1H, dd, J=9 Hz, J'=2 Hz, aromatic H ortho to —O—), 7.31 (1H, d, J=2 Hz, aromatic H ortho to —O—), 7.51 (1H, s, aromatic H ortho to NH.CO), 7.68 (1H, d, J=9 Hz, aromatic H meta to —O—), 7.73 (1H, d, J=7 Hz, CO.NH-cyclohexyl), 10.96 (1H, s, NH.CO), and 11.37 (1H, s, NH.CO).

EXAMPLE 19

N-Cyclohexyl-4-[(2,3-dihydro-1-methyl-2-oxo 1H-imidazo[4,5-b]quinolin-7-yl)oxy]butanamide

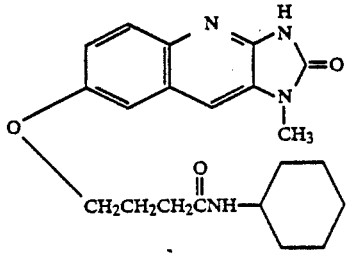

This compound, m.p. 282°–284° C., was prepared analogously to Example 15 from 4-[(2,3-dihydro-1-methyl-2-oxo-1H-imidazo[4,5-b]quinolin-7-yl)oxy]butanoic acid and cyclohexylamine.

Anal. Calcd. for $C_{21}H_{26}N_4O_3$: C, 65.95; H, 6.85; N, 14.65. Found: C, 65.87; H, 6.85; N, 14.70.

NMR (DMSO-d₆/CF₃CO₂H): delta 1.20 to 2.00 (10H, m, CH₂), 2.30 (2H, m, —O—CH₂.CH₂), 2.76 (2H, m, CH₂CO.NH), 3.57 (3H, s, N—CH₃), 3.88 (1H, m, CO.NH.CH), 4.24 (2H, m, —O—CH₂), 7.47 (2H, m, aromatic H ortho to —O—), 7.94 (1H, d, J=9 Hz, aromatic H meta to —O—) and 8.07 (2H, s, aromatic H ortho to NH.CO and NH.CO).

EXAMPLE 20

N-Cycloheptyl-4-[(2,3-dihydro-2-oxo-1H-imidazo[4,5-b]quinolin-7-yl)oxy]butanamide

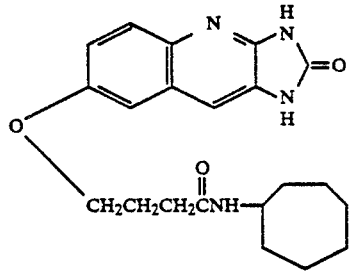

This compound, m.p. 314°–316°, was prepared analogously to Example 15 from 4-[(2,3-dihydro-2-oxo-1H-imidazo[4,5-b]quinolin-7-yl)oxy]butyric acid and N-cycloheptylamine.

Anal. Calcd. for $C_{21}H_{26}N_4O_4$: C, 65.95; H, 6.85; N, 14.65. Found: 66.05; H, 6.93; N, 14.76.

NMR (DMSO-d₆): delta 1.35 to 1.90 (12H, m, CH₂), 2.00 (2H, m, —O—CH₂.CH₂), 2.27 (2H, t, J=7 Hz, CH.CO.NH), 3.75 (1H, m, NH.CH), 4.05 (2H, t, J=6 Hz, —O—CH₂), 7.15 (1H, dd, J=9 Hz, J'=2.5 Hz, aromatic H ortho to —O—), 7.31 (1H, d, J=2.5 Hz, aromatic H ortho to —O—), 7.52 (1H, s, aromatic H ortho to NH.CO), 7.69 (1H, d, J=9 Hz, aromatic H meta to —O—), 7.78 (1H, d, J=8 Hz, CONH-cycloheptyl), 10.98 (1H, s, NH.CO), and 11.38 (1H, s, NH.CO).

EXAMPLE 21

N-Cyclohexyl-N-[4-[(2,3-dihydro-2-oxo-1H-imidazo[4,5-b]quinolin-7-yl)oxy]-1-oxobutyl]glycine Methyl Ester

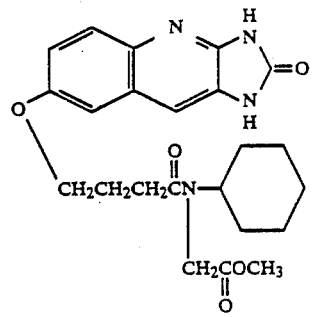

This compound obtained as a partial hydrate, m.p. 215°–218° C., was prepared analogous to Example 15 from 4-[(2,3-dihydro-2-oxo-1H-imidazo[4,5-b]quinolin-7-yl)oxo]butyric acid and N-cyclohexylglycine methyl ester.

Anal. Calcd. for $C_{23}H_{28}N_4O_5 \cdot 0.25H_2O$: C, 62.08; H, 6.46; N, 12.59; H₂O, 1.01. Found: C, 61.98; H, 6.24; N, 12.68; H₂O, 0.94.

NMR (DMSO-d₆): delta 1.05 to 1.80 (10H, m, CH₂), 2.06 (2H, bs, —O—CH₂.CH₂), 2.63 (2H, m, CH₂CON), 3.64 (3H, s, CO₂CH₃), 3.71 and 3.95 (2H, s, N—CH₂—CO₂CH₃ rotational isomers), 4.12 (2H, m, —O—CH₂), 4.19 (1H, s, CO.N—CH), 7.19 (1H, m, aromatic H ortho to —O—), 7.35 (1H, s, aromatic H ortho to —O—), 7.56 (1H, s, aromatic H ortho to NH.CO), 7.73 (1H, d, J=8.4 Hz, aromatic H meta to —O—), 11.01 (1H, s, NH.CO), and 11.43 (1H, s, NH.CO).

EXAMPLE 22

N-Cycloheptyl-N-methyl-4-[(2,3-dihydro-2-oxo-1H-imidazo[4,5-b]quinolin-7-yl)oxy]butanamide

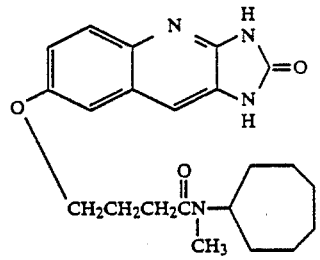

This compound obtained as the hydrochloride salt, m.p. 180°–182° C., was prepared analogous to Example 15 from 4-[(2,3-dihydro-2-oxo-1H-imidazo[4,5-b]quinolin-7-yl)oxy]butyric acid and N-methylcycloheptylamine.

Anal. Calcd. for $C_{22}H_{28}N_4O_3 \cdot HCl$: C, 61.03; H, 6.75; N, 12.94. Found: C, 60.70; H, 6.81; N, 13.06.

NMR (DMSO-d₆): delta 1.44–1.65 (12H, m, CH₂), 2.00 (2H, m, —O—CH₂.CH₂), 2.44 to 2.52 (2H, m, CH₂CON), 2.68 and 2.80 (3H, s, N-CH₃, rotational isomers), 3.81 and 4.46 (1H, s, CO.N-CH, rotational isomer), 4.08 (2H, m, —OCH₂, 7.22 (1H, d, J=9 Hz, aromatic H ortho to —O—), 7.41 (1H, s, aromatic H ortho to —O—), 7.66 (1H, s, aromatic H ortho to NH.CO), 7.79 (1H, d, J=9 Hz, aromatic H meta to —O—), and 11.30 (1H, s, NH.CO).

EXAMPLE 23

N-Cycloheptyl-4-[(2,3-dihydro-1-methyl-2-oxo-1H-imidazo[4,5-b]quinolin-7-yl)oxy]-N-methylbutanamide

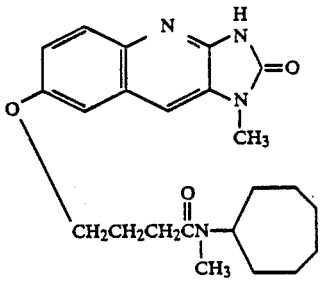

This compound, m.p. 234.5°–236.5° C., was prepared analogous to Example 15 from 4-[(2,3-dihydro-1-methyl-2-oxo-1H-imidazo[4,5-b]quinolin-7-yl)oxy]butanoic acid and N-methylcycloheptylamine.

Anal. Calcd. for $C_{23}H_{30}N_4O_3$: C, 67.29; H, 7.37; N, 13.65. Found: C, 66.93; H, 7.33; N, 13.90.

NMR (DMSO-$d_6$): delta 1.40 to 1.75 (12H, m, CH$_2$), 2.00 (2H, m, —O—CH$_2$.CH$_2$), 2.42 to 2.54 (2H, m, CH$_2$.CO.N), 2.68 and 2.81 (3H, s, N—CH$_3$ rotational isomers), 3.34 (3H, s, NH.CO.NCH$_3$), 3.80 and 4.45 (1H, m, CO.N—CH, rotational isomers), 4.08 (2H, m, —O—CH$_2$), 7.18 (1H, dd, J=9 Hz, J=2.6 Hz, aromatic H ortho to —O—), 7.29 (1H, d, J=2.6 Hz, aromatic H ortho to —O—), 7.64 (1H, s, aromatic H ortho to NH.CO), 7.71 (1H, d, J=9 Hz, aromatic H meta to —O—), and 11.58 (1H, s, NH.CO).

EXAMPLE 24

1-[4-[(2,3-Dihydro-2-oxo-1H-imidazo[4,5-b]quinolin-7-yl)oxy]-1-oxobutyl]piperidine

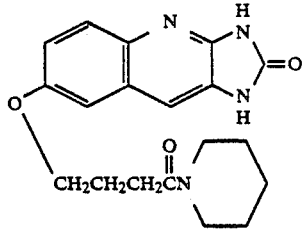

This compound, m.p. 284.5°–285.5° C., was prepared analogous to Example 15 from 4-[(2,3-dihydro-2-oxo-1H-imidazo[4,5-b]quinolin-7-yl)oxy]butyric acid and piperidine.

Anal. Calcd. for $C_{19}H_{22}N_4O_3$: C, 64.39; H, 6.26; N, 15.81. Found: C, 64.19; H, 6.33; N, 16.05.

NMR (DMSO-$d_6$): delta 1.41 to 1.56 (6H, CH$_2$), 2.00 (2H, m, —O—CH$_2$.CH$_2$), 2.49 (2H, t, J=7 Hz, CH$_2$.CO.N), 3.37 to 3.45 (4H, m, CH$_2$.N—CH$_2$), 4.08 (2H, t, J=6 Hz, —O—CH$_2$), 7.16 (1H, dd, J=9 Hz, J'=2 Hz, aromatic H ortho to —O—), 7.33 (1H, d, J=2 Hz, aromatic H ortho to —O—), 7.52 (1H, s, aromatic H ortho to NH.CO), 7.69 (1H, d, J=9 Hz, aromatic H meta to —O—), 10.96 (1H, s, NH.CO) and 11.38 (1H, s, NH.CO).

EXAMPLE 25

1-[4-[(2,3-Dihydro-1-methyl-2-oxo-1H-imidazo[4,5-b]quinolin-7-yl)oxy]-1-oxobutyl]piperidine

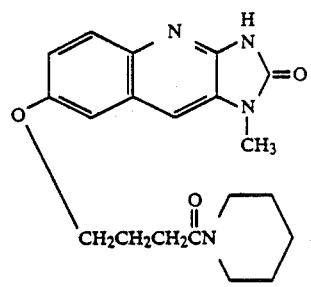

This compound, m.p. 215°–217° C., prepared analogous to Example 15 from 4-[(2,3-dihydro-1-methyl-2-oxo-1H-imidazo[4,5-b]quinolin-7-yl)oxy]butanoic acid and piperidine.

Anal. Calcd. for $C_{20}H_{24}N_4O_3$: C, 65.20; H, 6.57; N, 15.21. Found: C, 65.19; H, 6.57; N, 15.18.

NMR (DMSO-$d_6$): delta 1.40 to 1.70 (6H, m, CH$_2$), 2.02 (2H, m, —O—CH$_2$.CH$_2$), 2.49 (2H, t, J=7 Hz, CH$_2$.CO.N), 3.34 (3H, s, N—CH$_3$), 3.42 (4H, bs, CH$_2$.N—CH$_2$), 4.09 (2H, t, J=Hz, —O—CH$_2$), 7.17 (1H, dd, J=9 Hz, J'=2 Hz, aromatic H ortho to —O—), 7.28 (1H, d, J=2 Hz, aromatic H ortho to —O—), 7.59 (1H, s, aromatic H ortho to NH.CO), 7.71 (1H, d, J=9 Hz, aromatic H meta to —O—), and 11.49 (1H, s, NH.CO).

EXAMPLE 26

1-[4-[(2,3-Dihydro-2-oxo-1H-imidazo[4,5-b]quinolin-7-yl)oxy]-1-oxobutyl]-4-phenylpiperazine

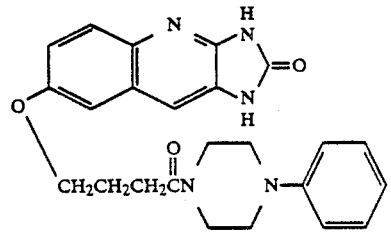

This compound, m.p. 277°–279° C., obtained as a dimethylformamide solvate was prepared analogous to Example 15 from 4-[(2,3-dihydro-2-oxo-1H-imidazo[4,5-b]quinolin-7-yl)oxy]butyric acid and 4-phenylpiperazine.

Anal. Calcd. for $C_{24}H_{25}N_5O_3.0.15\ C_3H_7NO$: C, 66.37; H, 5.93; N, 16.30. Found: C, 66.13; H, 5.92; N, 16.26.

NMR (DMSO-$d_6$): delta 2.04 (2H, q, J=7 Hz, —O—CH$_2$.CH$_2$), 2.57 (2H, t, J=7 Hz, CH$_2$.CO.N), 3.09 (4H, bs, CH$_2$.N—CH$_2$), 3.60 (4H, bs, CH$_2$), 4.10 (2H, t, J=6 Hz, —O—CH$_2$), 6.82 (1H, t, J=7 Hz, aromatic H, para to N), 6.95 (2H, d, J=8 Hz, aromatic H ortho to N), 7.15 to 7.24 (3H, m, 2 aromatic H meta to N and 1 aromatic H ortho to —O—), 7.34 (1H, d, J=2.7 Hz, aromatic H ortho to —O—), 7.51 (1H, s, aromatic H to NH.CO), 7.69 (1H, d, J=9 Hz, aromatic H meta to —O—), 10.96 (1H, s, NH.CO) and 11.35 (1H, s, NH.CO).

EXAMPLE 27

N-Cyclohexyl-5-[(2,3-dihydro-1-methyl-2-oxo-1H-imidazo[4,5-b]quinolin-7-yl)oxy]N-methylpentanamide

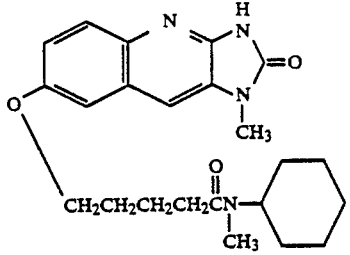

This compound obtained as a partial hydrate, m.p. 190°–192° C., was prepared analogous to Example 15 from 5-[(2,3-dihydro-1-methyl-2-oxo-1H-imidazo[4,5-b]quinolin-7-yl)oxy]pentanoic acid and N-methylcyclohexylamine.

Anal. Calcd. for $C_{23}H_{30}N_4O_3 \cdot 0.1H_2O$: C, 67.00; H, 7.38; N, 13.59; $H_2O$, 0.44. Found: C, 66.60; H, 7.37; N, 13.58; $H_2O$, 0.04.

NMR (DMSO-$d_6$): delta 1.00 to 1.90 (14H, m, $CH_2$), 2.35 (2H, m, $CH_2.CO.N$), 2.68 and 2.79 (3H, s, N—$CH_3$, rotational isomers), 3.34 (3H, s, NH.CO.N$CH_3$), 3.63 and 4.29 (1H, m, N—CH, rotational isomers), 4.07 (2H, m, —O—$CH_2$), 7.16 (1H, dd, J=9 Hz, J'=2.4 Hz, aromatic H ortho to —O—), 7.28 (1H, d, J=2.4 Hz, aromatic H ortho to —O—), 7.62 (1H, s, aromatic H ortho to NH.CO), 7.71 (1H, d, J=9 Hz, aromatic H meta to —O—), and 16.32 (1H, s, NH.CO).

EXAMPLE 28

N-Cycloheptyl-5-[(2,3-dihydro-1-methyl-2-oxo-1H-imidazo[4,5-b]quinolin-7-yl)oxy]-N-methylpentanamide

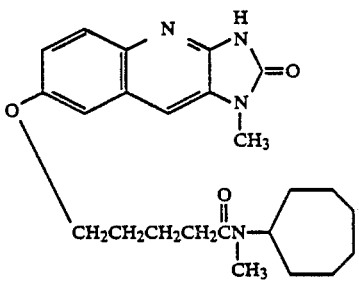

This compound obtained as a partial hydrate, m.p. 183°–185° C., was prepared analogous to Example 15 from 5-[(2,3-dihydro-1-methyl-2-oxo-1H-imidazo[4,5-b]quinolin-7-yl)oxy]pentanoic acid and N-methylcycloheptylamine.

Anal. Calcd. for $C_{24}H_{32}N_4O_3 \cdot 0.1H_2O$: C, 67.62; H, 7.62; N, 13.15; $H_2O$, 0.42. Found: C, 67.48; H, 7.52; N, 13.22; $H_2O$, 0.37.

NMR (DMSO-$d_6$): delta 1.40 to 1.95 (16H, m, C$CH_2$), 2.32 and 2.43 (2H, t, J=7 Hz, $CH_2.CO.N$, rotational isomers), 2.67 and 2.79 93H, s, N—$CH_3$, rotational isomers), 3.35 (3H, s, NH.CO.N$CH_3$), 3.79 and 4.48 (1H, m, N—CH, rotational isomers), 4.05 (2H, m, —O—$CH_2$), 7.16 (1H, d, J=9 Hz, aromatic H, ortho to —O—), 7.25 (1H, d, J=1.5 Hz, aromatic H ortho to —O—), 7.57 (1H, s, aromatic H ortho to NH.CO), 7.73 (1H, d, J=9 Hz, aromatic H meta to —O—) and 11.61 (1H, s, NH.CO).

EXAMPLE 29

Ethyl 1-[4-[(2,3-Dihydro-2-oxo-1H-imidazo[4,5-b]quinolin-7-yl)oxy]-1-oxobutyl]-4-piperidinecarboxylate

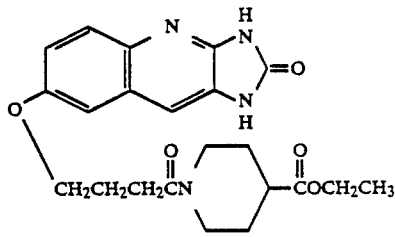

This compound, m.p. 251°–253° C., was prepared analogous to Example 15 from 4-[(2,3-dihydro-2-oxo-1H-imidazo[4,5-b]quinolin-7-yl)oxy]butyric and ethyl 4-piperidinecarboxylate.

Anal. Calcd. for $C_{22}H_{26}N_4O_5$: C, 61.96; H, 6.15; N, 13.14 Found C, 61.78; H, 6.13; N, 13.10.

NMR (DMSO-$d_6$): data 1.18 (3H, t, J=7 Hz, O.$CH_2.CH_3$), 1.35 to 1.90 (7H, m, $CH_2$ of ring), 2.02 (2H, m, O—$CH_2.CH_2$), 2.50 (2H, m, $CH_2.CO.N$), 2.74 and 3.10 (2H, t, J=12 Hz, one each of $CH_2$—N.$CH_2$), 3.88 and 4.31 (2H, d, J=12 Hz, one each of $CH_2$—N.$CH_2$), 4.03 to 4.09 (4H, m, O$CH_2$), 7.17 (1H, dd, J=9 Hz, J'=2 Hz, aromatic H ortho to —O—), 7.33 (1H, d, J=2 Hz, aromatic H ortho to —O—), 7.53 (1H, s, aromatic H ortho to NH.CO), 7.71 (1H, d, J=9 Hz, aromatic H meta to —O—), 10.95 (1H, s, NH.CO) and 11.37 (1H, s, NH.CO).

EXAMPLE 30

N-Cyclohexyl-N-methyl-4-[(2,3-dihydro-2-oxo-1H-imidazo[4,5-b]quinolin-7-yl)oxy]butanamide

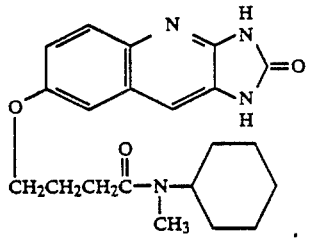

A solution of 5-[[5-[3-[[(cyclohexyl)methylamino]-carbonyl]propoxy]-2-nitrophenyl]methylene]imidazolindine-2,4-dione hydrate (19.5 g, 45 mmol) in dimethylformamide (500 mL) was hydrogenated at 60 p.s.i. over 10% palladium on charcoal (2 g) in a low pressure hydrogenation apparatus. After 18 hours, the mixture was filtered through kieselguhr and the solvent removed in vacuo. The residue was dissolved in refluxing methanol (400 mL) and iodine (10 g, 39 mmol) added portionwise over 15 minutes. The mixture was refluxed for 15 minutes, concentrated in vacuo to about 75 mL and diluted with 10% sodium thiosulfate solution (about 400 mL) to afford a khaki precipitate. Crystallization from ethyl acetate afforded the title product (5 g, 28%) which was dissolved in 10% hydrogen chloride in methanol and precipitated by the addition of diethyl ether to afford partially hydrated N-cyclohexyl-N-methyl-4-[(2,3- dihydro-2-oxo-1H-imidazo[4,5-b]quinolin-7-yl)-oxy]-butanamide hydrochloride (4.78 g, 87%), m.p. 198°–201° C.

Anal. Calcd. for C₂₁H₂₆N₄O₃.HCl.0.4H₂O: C, 59.19; H, 6.58; N, 13.15; H₂O, 1.69. Found: C, 59.27; H, 6.42; N, 12.91; H₂O, 1.44.

NMR (DMSO-d₆): delta 0.80 to 2.30 (12H, m, —CH₂—), 2.55 (2H, m, —CH₂CO), 2.72 and 2.83 (3H, singlets, N—CH₃), 3.65 (1H, m, NCH), 4.12 (2H, t, J=6 Hz, OCH₂), 7.26 (1H dd, J=9 Hz, J'=3 Hz, aromatic H ortho to —O—), 7.48 (1H, d, J=3 Hz, aromatic H ortho to —O—), 7.81 (1H, s, aromatic H ortho to NH.CO), 7.96 (1H, d, J=9 Hz, aromatic H meta to —O—), 10.55 (1H, bs, NH) and 11.68 (1H, bs, NH).

EXAMPLE 31

N-Cyclohexyl-N-methyl-4-[(2,3-dihydro-1-methyl-2-oxo-1H-imidazo[4,5-b]quinolin-7-yl)oxo]butanamide

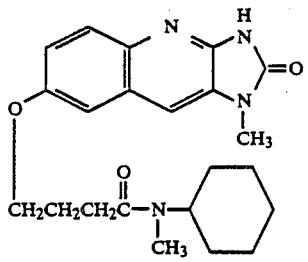

A solution of N-cyclohexyl-N-methyl-4-[3-[(1-methyl-2,4-dioxoimidazolidin-5-ylidene)methyl]-4-nitrophenoxy]butanamide (9.5 g, 21 mmol) in dimethylformamide (250 mL) was hydrogenated at 60 p.s.i. over 10% palladium on charcoal (1 g), in a low pressure hydrogenation apparatus. After 18 hours further catalyst (0.5 g) was added and hydrogenation continued for a further 23 hours. The mixture was filtered through kieselguhr, the solvent removed in vacuo and residue dissolved in methanol (200 mL). Iodine (5 g) was added in small portions over 5 minutes and the mixture refluxed for 10 minutes before being concentrated to about 50 mL. The mixture was diluted with 10% sodium thiosulfate solution (100 mL) and 10% sodium carbonate solution (100 mL) and extracted with dichloromethane to give a solid which was dissolved in dichloromethane, filtered and diluted with diethyl ether to precipitate partially hydrated N-(cyclohexyl)-N-methyl-4-[(2,3-dihydro-1-methyl-2-oxo-1H-imidazo[4,5-b]quinolin-7-yl)oxy]-butanamide (4.50 g, 53%) m.p. 218°–220° C.

Anal. Calcd. for C₂₂H₂₈N₄O₃.0.4H₂O: C, 65.46; H, 7.19; N, 13.88; H₂O, 1.79. Found: C, 65.07; H, 6.87; N, 13.74; H₂O, 0.58.

NMR (DMSO-d₆): delta 1.00 to 2.35 (12H, m. —CH₂—), 2.55, (2H, m. CH₂.CO), 2.80 and 2.86 (3H, singlets, NCH₃ of side chain), 3.40 (3H, s, NCH₃ of ring), 4.12 (3H, t, J=6 Hz, O—CH₂), 7.06 to 7.26 (2H, m, aromatic ortho to —O—), 7.30 (1H, s, aromatic H ortho to NH.CO) and 7.81 (1H, d, J=9 Hz, aromatic H meta to —O—).

EXAMPLE 32

N-Cyclohexyl-N-methyl-5-[(2,3-dihydro-2-oxo-1H-imidazo[4,5-b]quinolin-7-yl)oxo]pentanamide

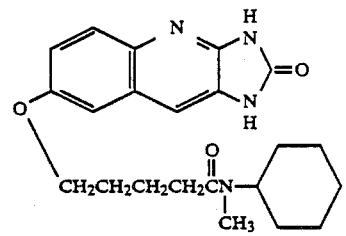

This compound obtained as a partial hydrate, m.p. 207°–210° C., was prepared analogous to Example 30 from N-cyclohexyl-N-methyl-5-[3-[(2,4-dioxoimidazolidin-5-ylidene)methyl]-4-nitrophenoxy]pentanamide.

Anal. Calcd. for C₂₂H₂₈N₄O₃0.11H₂O: C, 66.31; H, 7.14; N, 14.06; H₂O, 0.50. Found: C, 65.92; H, 7.03; N, 14.10; H₂O, 0.13.

NMR (DMSO-d₆): delta 1.29 to 1.79 (14H, m, CH₂), 2.35 to 2.41 (2H, m, CH₂CO), 2.68 and 2.79 (3H, s, N—CH₃, rotational isomers), 3.60 and 4.27 (1H, m, CO.N—CH, rotational isomers), 4.07 (2H, m, —O—CH₂), 7.15 (1H, d, J=9 Hz, aromatic H ortho to —O—), 7.33 (1H, s, aromatic H ortho to —O—), 7.52 (1H, s, aromatic H ortho to NH.CO), 7.70 (1H, d, J=9 Hz, aromatic H meta to —O—), 10.95 (1H, s, NH.CO) and 11.36 (1H, s, NH.CO).

EXAMPLE 33

N-Cycloheptyl-N-methyl-5-[(2,3-dihydro-2-oxo-1H-imidazo[4,5-b]quinolin-7-yl)oxy]pentanamide

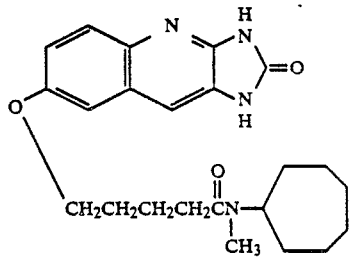

This compound obtained as a partial hydrate, m.p. 189°–191° C., was prepared analogous to Example 30 from N-cyclopheptyl-N-methyl-5-[[4-nitro-3-(2,4-dioxoimidazolidin-5-yl)methylene]phenoxy]pentanamide.

Anal. Calcd. for C₂₃H₃₀N₄O₃.0.15H₂O: C, 66.85; H, 7.39; N, 13.56; H₂O, 0.65. Found: C, 66.64; H, 7.31; N, 13.50; H₂O, 0.56.

NMR (DMSO-d₆): delta 1.30 to 1.85 (16H, m, CH₂), 2.32 and 2.44 (2H, t, CH₂CON, rotational isomers) 2.65 and 2.79 (3H, s, N—CH₃, rotational isomers), 3.77 and 4.43 (1H, m, N—CH, rotational isomers), 4.06 (2H, m, —O—CH₂), 7.15 (1H, d, J=9 Hz, aromatic H ortho to —O—), 7.32 (1H, s, aromatic H ortho —O—), 7.51 (1H, s, aromatic H ortho to NH.CO), 7.68 (1H, d, J=9 Hz, aromatic H meta to —O—), 10.96 (1H, s, NH.CO) and 11.36 (1H, s, NH.CO).

EXAMPLE 34

7-[(2-Diethylamino)ethoxy]-1,3-dihydro-2H-imidazo[4,5-b]quinolin-2-one

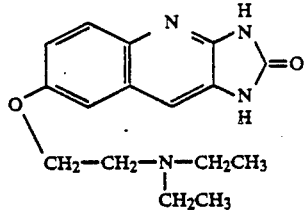

A solution of 5-[[5-[(2-diethylamino)ethoxy]-2-nitrophenyl]methylene]-2,4-imidazolidinedione (7 g, 20 mmol) in dimethylformamide (130 mL) was hydrogenated at 60 p.s.i. over 10% palladium on charcoal (0.7 g) in a low pressure hydrogenation apparatus. After 22 hours, the mixture was filtered through kieselguhr, the solvent evaporated and the residue dissolved in refluxing methanol (100 mL). Iodine (5.12 g, 20 mmol) was added portionwise over 5 minutes, the mixture refluxed 30 minutes and then concentrated in vacuo to about 50 mL. 10% Sodium thiosulfate solution (about 200 mL) and 10% sodium carbonate solution (until neutral) was added and the mixture stirred for 20 minutes before being filtered. The collected solid (2.2 g, 37%) was dissolved in 10% hydrogen chloride in methanol. Addition of diethyl ether precipitated 7-[(2-diethylamino)ethoxy]-1,3-dihydro-2H-imidazo[4,5-b]quinolin-2-one dihydrochloride hemihydrate (2.20 g, 79%), m.p. 250°-255° C. (dec).

Anal. Calcd. for $C_{16}H_{20}N_4O_2 \cdot 2HCl \cdot 0.5H_2O$: C, 50.28; H, 6.07; N, 14.66; $H_2O$, 2.36. Found: C, 50.18; H, 6.04; N, 14.57.

NMR (DMSO-$d_6$) delta 1.33 (6H, bs, ($CH_2CH_2CH_3$)$_2$), 3.28 (4H, bs, N—($CH_2CH_3$)$_2$), 3.60 (2H, bs, N—$CH_2CH_2O$), 4.57 (2H, bs, $OCH_2$), 7.29 (1H, d, J=8 Hz, aromatic H ortho to —O—), 7.54 (1H, s, aromatic H ortho to —O—), 7.75 (1H, s, aromatic H ortho to $\overline{N}H.CO$), 7.90 (1H, d, J=8 Hz, aromatic H meta to —O—).

EXAMPLE 35

7-[4-(Phenylsulfonyl)butoxy]-1,3-dihydro-2H-imidazo[4,5-b]quinolin-2-one

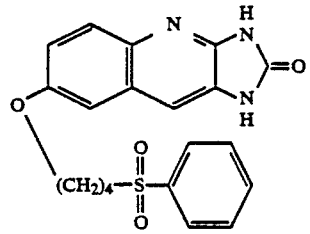

A solution of 5-[[2-nitro-5-[4-(phenylsulfonyl)butoxy]phenyl]methylene]-2,4-imidazolidinedione (4.12 g, 9.1 mmol) in dimethylformamide (125 mL) was hydrogenated at 60 p.s.i. over 10% palladium on charcoal (1.25 g) in a low pressure hydrogenation apparatus. After 18 hours, the mixture was filtered through kieselguhr, the solvent evaporated and the residue dissolved in dimethylformamide (125 mL) and resubjected to hydrogenation over 10% palladium on charcoal (1.2 g). After 4 hours, the mixture was filtered through kieselguhr, concentrated in vacuo and the residue dissolved in refluxing methanol (150 mL). Iodine (2.35 g, 9 mmol) was added and the mixture refluxed for 1 hour, cooled and diluted with 10% sodium thiosulfate solution and 10% potassium carbonate solution. The mixture was stirred for 10 minutes, filtered and the solid washed with water and dried at 90° C. in vacuo. Crystallization from acetonitrile/dimethylformamide/water afforded 7-[4-(phenylsulfonyl)butoxy]-1,3-dihydro-2H-imidazo[4,5-b]quinolin-2-one as a partial hydrate (1.90 g, 51%), m.p. 258° C. (dec.).

Anal. Calcd. for $C_{20}H_{19}N_3O_4S \cdot 0.2H_2O$: C, 59.90; H, 4.88; N, 10.48; $H_2O$, 0.90. Found: C, 59.62; H, 4.79; N, 10.14; $H_2O$, 0.61.

NMR (DMSO-$d_6$) delta 1.65 to 2.00 (4H, m, $CH_2$), 3.42 (2H, t, J=8 Hz, $CH_2.SO_2Ph$), 4.03 (2H, t, J=5.5 Hz, —O—$CH_2$—), 7.09 (1H, dd, J=9 Hz, J'=2 Hz, aromatic H ortho to —O—), 7.29 (1H, d, J=2 Hz, aromatic H ortho to —O—), 7.48 (1H, s, aromatic H ortho to —$\overline{N}H.CO$—), 7.50 to 8.10 (6H, aromatic H), 10.94 (1H, bs, $\underline{NH}$), and 11.35 (1H, s, $\underline{NH}$).

EXAMPLE 36

7-[4-(1-Cyclohexyl-1H-tetrazol-5-yl)butoxy]-1,3-dihydro-2H-imidazo[4,5-b]quinolin-2-one

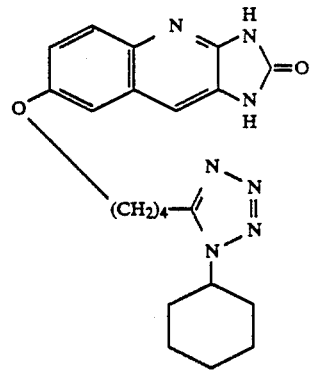

A solution of 5-[[5-[4-(1-cyclohexyl-1H-tetrazol-5-yl)butoxy]-2-nitrophenyl]methylene]-2,4-imidazolidinedione (12 g, 26 mmol) in dimethylformamide (200 mL) was hydrogenated at 55 p.s.i. over 10% palladium on charcoal (1.2 g) in a low pressure hydrogenation apparatus. After 40 hours, the mixture was filtered through kieselguhr, the solvent evaporated and the residue suspended in refluxing methanol. Iodine (6.69 g, 26 mmol) was added portionwise over 4 minutes, reflux continued for 10 minutes, and the mixture then concentrated in vacuo to approximately 70 mL. 10% Sodium thiosulate solution and 10% sodium carbonate solution was added, the mixture stirred for 5 minutes and a solid filtered off, washed with water and dried in air. This was dissolved in hot dimethylformamide and water added to precipitate a solid (4.80 g) which was dissolved in 10% hydrogen chloride in methanol. The methanol was removed and the residue crystallized from ethanol to give the hydrochloride salt of 7-[4-(1-cyclohexyl-1H-tetrazol-5-yl)butoxy]-1,3-dihydro-2H-imidazo[4,5-b]quinolin-2-one (2.16 g, 18% overall), m.p. 288°-291° C.

Anal. Calcd. for $C_{21}H_{25}N_7O_2 \cdot HCl$: C, 56.82; H, 5.91; N, 22.09. Found: C, 56.81; H, 5.85; N, 22.06.

NMR (DMSO-$d_6$) delta 1.10 to 2.10 (14H, m, $CH_2$), 3.03 (2H, t, J=7 Hz, $CH_2$—C≡N), 4.15 (2H, bs, $OCH_2$), 4.46 (1H, m, N—C$\underline{H}$), 7.26 (1H, dd, J=9 Hz, J'=3 Hz, aromatic $\underline{H}$ ortho to —O—), 7.47 (1H, d, J=3 Hz, aromatic H ortho to —O—), 7.77 (1H, s, aromatic $\underline{H}$ ortho to N$\overline{H}$.CO), 7.92 (1H, d, J=9 Hz, aromatic $\underline{H}$ meta to —O—), 11.59 (3H, m, N$\underline{H}$+H+).

EXAMPLE 37

7-(2-Ethoxyethoxy)-1,3-dihydro-2$\underline{H}$-imidazo[4,5-b]quinolin-2-one

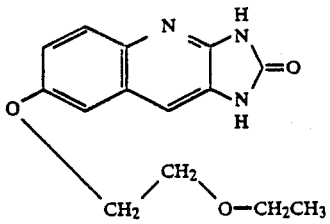

A solution of 5-[[5-(2-ethoxyethoxy)-2-nitrophenyl]methylene]-2,4-imidazolidinedione (10.60 g, 33 mmol) in dimethylformamide (120 mL) was hydrogenated over 10% palladium on charcoal (1 g) at 50 p.s.i. in a low pressure hydrogenation apparatus. After 23 hours, the mixture was filtered through kieselguhr and the solvent evaporated to leave a solid which was suspended in refluxing methanol (200 mL) and treated with iodine (8.38 g, 33 mmol) added portionwise. After 15 minutes the mixture was concentrated to about 50 mL and diluted with 10% sodium thiosulfate solution and 10% sodium carbonate solution. The mixture was stirred for 15 minutes and the solid filtered off, washed with water and dried in air before being dissolved in a solution of 10% hydrogen chloride in methanol. Addition of diethyl ether precipitated 7-(2-ethoxyethoxy)-1,3-dihydro-2$\underline{H}$-imidazo[4,5-b]quinolin-2-one hydrochloride (4.52 g, 56%), m.p. 290°-293° C. (dec.).

Anal. Calcd. for $C_{14}H_{15}N_3O_3$.HCl: C, 54.29; H, 5.21; N, 13.57. Found: C, 54.41; H, 5.23; N, 13.65.

NMR (DMSO-$d_6$): delta 1.16 (3H, t, J=7 Hz, OCH$_2$C$\underline{H}_3$), 3.54 (2H, q, J=7 Hz, OC$\underline{H}_2$CH$_3$), 3.77 (2H, bs, OC$\underline{H}_2$), 4.19 (2H, bs, aromatic—O—C$\underline{H}_2$), 7.31 (1H, dd, J=9 Hz, J'=2 Hz, aromatic H ortho to —O—), 7.50 (1H, d, J=2 Hz, aromatic $\underline{H}$ ortho to —O—), 7.86 (1H, s, aromatic $\underline{H}$ ortho to N$\overline{H}$.CO), and 7.97 (1H, d, J=9 Hz, aromatic $\underline{H}$ meta to —O—).

EXAMPLE 38

1,3-Dihydro-7-(3-hydroxypropoxy)-2$\underline{H}$-imidazo[4,5-b]quinolin-2-one

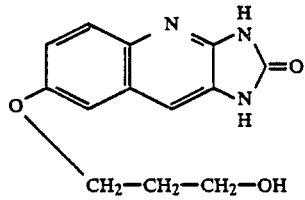

A solution of 5-[[2-nitro-5-[3-[(tetrahydro-2$\underline{H}$-pyran-2-yl)oxy]propoxy]phenyl]methylene]-2,4-imidazolidinedione (19.14 g, 49 mmol) in dimethylformamide (150 mL) was hydrogenated over 10% palladium on charcoal (2 g) at 55 p.s.i. in a low pressure hydrogenation apparatus. After 23 hours, the mixture was filtered through kieselguhr and concentrated in vacuo. The resultant yellow solid was dissolved in refluxing methanol (300 mL) and iodine (11.74 g, 49 mmol) added portionwise. After 15 minutes, the mixture was concentrated to dryness and the residue diluted with 10% sodium thiosulfate solution and 10% sodium carbonate solution. The solid was filtered off, washed with water and dried in air. Crystallization from aqueous dimethylformamide afforded 1,3-dihydro-7-(3-hydroxypropoxy)-2$\underline{H}$-imidazo[4,5-b]quinolin-2-one (4.22 g, 33%), m.p. 343°-345° C. (dec.).

Anal. Calcd. for $C_{13}H_{13}N_3O_3$: C, 60.23; H, 5.06; N, 16.21. Found: C, 60.25; H, 5.08; N, 15.84.

NMR (DMSO-$d_6$): delta 1.96 (2H, quintet, J=6 Hz, OCH$_2$C$\underline{H}_2$CH$_2$OH), 3.64 (2H, t, J=6 Hz, C$\underline{H}_2$OH), 4.15 (2H, t, J=6 Hz, aromatic O—C$\underline{H}_2$), 4.68 (1H, bs, O$\underline{H}$), 7.18 (1H, dd, J=8 Hz, J'=2.5 Hz, aromatic $\underline{H}$ ortho to —O—), 7.35 (1H, d, J=2.5 Hz, aromatic $\underline{H}$ ortho to —O—), 7.56 (1H, s, aromatic $\underline{H}$ ortho to —NCO), and 7.71 (1H, d, J=8 Hz, aromatic $\underline{H}$ meta to —O—).

EXAMPLE 39

1,3-Dihydro-7-(4-oxopentoxy)-2$\underline{H}$-imidazo[4,5-b]quinolin-2-one

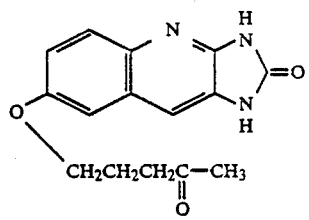

A solution of 5-[[5-[3-(2-methyl-1,3-dioxolan-2-yl)propoxy]-2-nitrophenyl]methylene]-2,4-imidazolidinedione (34.7 g, 92 mmol) in dimethylformamide (500 mL) was hydrogenated over 10% palladium on charcoal (3.5 g) at 200 p.s.i. in a low pressure hydrogenator. After 18 hours, the mixture was filtered through kieselguhr and concentrated in vacuo to afford a beige solid which was suspended in refluxing methanol (500 mL). Iodine (23.3 g, 92 mmol) was added portionwise and the mixture heated at reflux for a further 30 minutes before being cooled and diluted with 10% sodium thiosulfate solution (230 mL) and 10% sodium carbonate solution (75 mL). The mixture was concentrated to a volume of approximately 400 mL, the precipitate filtered off, washed with water and dried in vacuo of 70° C. to afford 1,3-dihydro-7-(4-oxopentoxy)-2$\underline{H}$-imidazo[4,5-b]quinolin-2-one (22.1 g, 84%). An analytical sample was prepared by crystallizing a 10 g portion from aqueous dimethylformamide to give 7.8 g of pure material which had m.p. 294°-296° C. (dec.).

Anal. Calcd. for $C_{15}H_{15}N_3O_3$: C, 63.15; H, 5.30; N, 14.73. Found: C, 62.69; H, 5.09; N, 14.44.

NMR (DMSO-$d_6$): delta 1.97 (2H, quintet, J=7 Hz, —CH$_2$C$\underline{H}_2$CO), 2.14 (3H, s, C$\underline{H}_3$.CO), 2.64 (2H, t, J=7 Hz, C$\underline{H}_2$CO), 4.83 (2H, t, J=7 Hz, OC$\underline{H}_2$), 7.15 (1H, d, J=9 Hz, aromatic $\underline{H}$ ortho to —O—), 7.31 (1H, s, aromatic $\underline{H}$ ortho to —O—), 7.53 (1H, s, aromatic $\underline{H}$ ortho to NH.CO) and 7.70 (1H, d, J=9 Hz, aromatic $\underline{H}$ meta to —O—).

EXAMPLE 40

1,3-Dihydro-7-(4-hydroxypentoxy)-2H-imidazo[4,5-b]quinolin-2-one

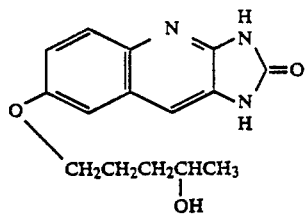

Sodium borohydride (1.00 g, 26 mmol) was added portionwise to a stirred suspension of 1,3-dihydro-7-(4-oxopentoxy)-2H-imidazo[4,5-b]quinolin-2-one (3.70 g, 13 mmol) in methanol (85 mL) and dimethylformamide (85 mL). The mixture was stirred at room temperature for 3 hours and then the solvent removed in vacuo. The residual oil was triturated with water (50 mL) and the solid material filtered off, washed with water and dried in air. Crystallization from aqueous dimethylformamide followed by trituration with methanol afforded 1,3-dihydro-7-(4-hydroxypentoxy)-2H-imidazo[4,5-b]-quinolin-2-one (3.20 g, 86%), m.p. 301°-303° C.

Anal. Calcd. for $C_{15}H_{17}N_3O_3$: C, 62.71; H, 5.96; N, 14.62. Found: C, 62.76; H, 5.67; N, 14.67.

NMR (DMSO-$d_6$): delta 1.14 (3H, d, J=6 Hz, CHOH.CH$_3$), 1.53 (2H, m, CH$_2$), 1.70 to 2.00 (2H, m, CH$_2$), 3.76 (1H, m, CHOH), 4.05 (2H, t, J=6 Hz, aromatic —O—CH$_2$), 4.58 (1H, bs, OH), 7.20 (1H, d, J=9 Hz, aromatic H ortho to —O—), 7.34 (1H, s, aromatic H ortho to —O—), 7.60 (1H, s, aromatic H ortho to NH.CO), and 7.75 (1H, d, J=9 Hz, aromatic H meta to —O—).

EXAMPLE 41

1,3-Dihydro-7-[[3-(1-methylethyl)-2-oxo-5-oxazolidinyl]methoxy]-2H-imidazo[4,5-b]quinolin-2-one

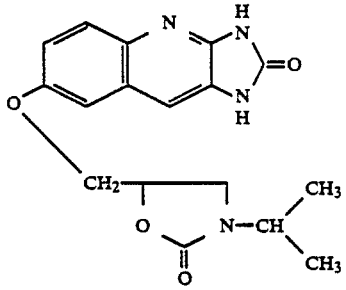

A solution of 5-[[5-[[[3-(1-methylethyl)-2-oxooxazolidin-5-yl]methyl]oxy]-2-nitrophenyl]methylene]-2,4-imidazolidinedione (8.80 g, 22 mmol) in dimethylformamide (150 mL) was hydrogenated at 60 p.s.i. over 10% palladium on charcoal (0.88 g) in a low pressure hydrogenation apparatus. After 21 hours, the mixture was filtered through kieselguhr and the solvent evaporated in vacuo at about 40° C. to leave a foamy solid. Methanol (180 mL) was added, the mixture heated to reflux and iodine (5.72 g 22 mmol) added portionwise over 15 minutes. After refluxing for a further 15 minutes, the mixture was concentrated to about 50 mL and diluted with 10% sodium sulfate solution and 10% sodium carbonate solution. A grey solid was filtered off, washed with water and air dried to give (4.18 g, 54%) of product. Three further crops amounting to (3.41 g, 46%) were subsequently collected. An analytical sample was purified by dissolving 2 g in 10% hydrochloric acid in methanol. Addition of diethyl ether afforded 1,3-dihydro-7-[[3-(1-methylethyl)-2-oxo-5-oxazolidinyl]methoxy]-2H-imidazo[4,5-b]quinolin-2-one hydrochloride (1.1 g, 50%) m.p. 264°-266° C.

Anal. Calcd. for $C_{17}H_{18}N_4O_4.HCl$: C, 53.90; H, 5.06; N, 14.80. Found: C, 53.60; H, 5.12; N, 14.68.

NMR (DMSO-$d_6$): Delta 1.16 and 1.18 (6H, d, J=7 Hz, CH.(CH$_3$)$_2$), 3.44 (1H, dd, J=8.5 Hz, J'=6 Hz one of N—CH$_2$), 3.72 (1H, t, J=9 Hz, one of N—CH$_2$), 3.95 (1H, septuplet, J=7 Hz, NCH(CH$_3$)$_2$, 4.15 to 4.40 (2H, m, OCH$_2$), 4.97 (1H, m, CH.OCO), 2.28 (1H, dd, J=9 Hz, J'=2 Hz, aromatic H ortho to —O—), 7.52 (1H, d, J=2 Hz, aromatic H ortho to —O—), 7.79 (1H, s, aromatic H ortho to NH.CO), 7.94 (1H, d, J=9 Hz, aromatic H meta to —O—).

EXAMPLE 42

7-[[3-(1,1-Dimethylethyl)-2-oxooxazolidin-5-yl]methoxy]-1H-imidazo[4,5-b]quinolin-2(3H)-one

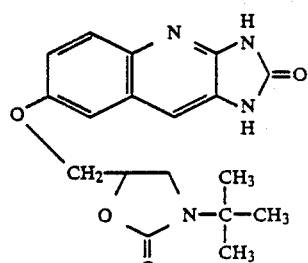

This compound, m.p. 257°-260° C. (dec.), obtained as partial hydrate hydrochloride salt was prepared analogous to Example 41 from 5-[[5-[[3-(1,1-dimethylethyl)-2-oxooxazolidin-5-yl)-methoxy]-2-nitrophenyl]methylene]imidazolidine-2,4-dione.

Anal. Calcd. for $C_{18}H_{20}N_4O_4.HCl.0.2H_2O$: C, 54.54; H, 5.45; N, 14.14; H$_2$O, 0.91. Found: C, 54.40; H, 5.31; N, 14.05; H$_2$O, 1.21.

NMR (DMSO-$d_6$): delta 1.37 (9H, s, C(CH$_3$)$_3$), 3.56 (1H, t, J=7 Hz, N—CH$_2$), 3.84 (1H, t, J=7 Hz, N—CH$_2$), 4.28 (2H, m, —O—CH$_2$), 4.85 (1H, bs, C—O—CH), 7.28 (1H, d, J=9 Hz, aromatic H ortho to —O—), 7.52 (1H, s, aromatic H ortho to —O—), 7.78 (1H, s, aromatic H ortho to —NH.CO—), 7.94 (1H, d, J=9 Hz, aromatic H meta to —O—), 11.00 (1H, bs, NH), 11.72 (1H, s, NH), 11.72 (1H, s, NH).

EXAMPLE 43

1,3-Dihydro-7-[2-hydroxy-3-[(1-methylethyl)amino]-propoxy]-2H-imidazo[4,5-b]quinolin-2-one

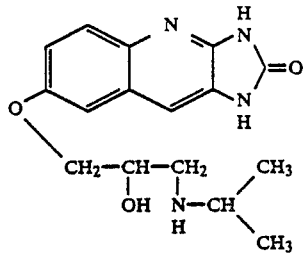

A mixture of 1,3-dihydro-7-[[3-(1-methylethyl)-2-oxo-5-oxazolidinyl]methoxy]-2H-imidazo[4,5-b]quinolin-2-one (3.00 g, 8.8 mmol) and 2N sodium hydroxide solution (25 mL) was refluxed for 5.5 hours and then neutralized by addition of dilute hydrochloric acid solution. A grey solid (2.15 g, 77%) was filtered off, washed with water and air dried. Crystallization from methanol afforded 1,3-dihydro-7-[2-hydroxy-3-[(1-methylethyl)amino]propoxy]-2H-imidazo[4,5-b]quinolin-2-one as a partial hydrate (1.53 g, 55%), m.p. 262°–264° C.

Anal. Calcd. for $C_{16}H_{20}N_4O_3.0.2H_2O$: C, 60.07; H, 6.43; N, 17.52; $H_2O$, 1.13. Found: C, 59.73; H, 6.38; N, 17.25; $H_2O$, 1.17.

NMR (DMSO-$d_6$): delta 1.15 (6H, d, J=7 Hz, CH.(CH$_3$)$_2$), 2.50 to 3.00 (3H, m, C$\overline{H}_2$.N—CH), 4.00 to 4.20 (3$\overline{H}$, m, OCH$_2$.CH.OH), 7.10 to 7.50 (6$\overline{H}$, m, aromatic H, (NH)$_3$ $\overline{OH}$), 7.61 (1H, s, aromatic H ortho to NH.C$\overline{O}$), 7.79 (1$\overline{H}$, d, J=6 Hz, aromatic $\overline{H}$ meta to —O—).

EXAMPLE 44

Additional compounds of Formula III (Formula I wherein Y is $CO_2H$) illustrated below may be prepared from the hydantoin intermediates of Example 3 according to the procedure of Example 4.

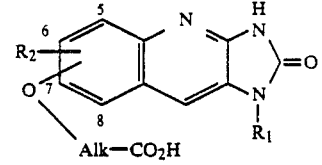

(III)

| Entry | $R_1$ | $R_2$ Position | $R_2$ Radical | O—Alk—Y Position | —Alk— |
|---|---|---|---|---|---|
| 44-1 | H | 8 | Cl | 7 | (CH$_2$)$_3$ |
| 44-2 | H | 5 | Cl | 7 | (CH$_2$)$_3$ |
| 44-3 | H | 6 | Cl | 7 | (CH$_2$)$_3$ |
| 44-4 | H | 5 | F | 7 | (CH$_2$)$_3$ |
| 44-5 | H | 8 | F | 7 | (CH$_2$)$_3$ |
| 44-6 | H | 8 | Me | 7 | (CH$_2$)$_3$ |
| 44-7 | H | 7 | F | 8 | (CH$_2$)$_3$ |
| 44-8 | H | 5 | Cl | 8 | (CH$_2$)$_3$ |
| 44-9 | H | 6 | F | 8 | (CH$_2$)$_3$ |
| 44-10 | H | — | H | 8 | (CH$_2$)$_3$ |
| 44-11 | H | 6 | Me | 8 | (CH$_2$)$_3$ |
| 44-12 | H | 7 | F | 8 | (CH$_2$)$_3$ |
| 44-13 | H | — | H | 5 | (CH$_2$)$_3$ |
| 44-14 | H | 7 | Me | 5 | (CH$_2$)$_3$ |
| 44-15 | H | 7 | F | 6 | (CH$_2$)$_3$ |
| 44-16 | H | 7 | Cl | 6 | (CH$_2$)$_3$ |
| 44-17 | H | — | H | 6 | (CH$_2$)$_3$ |
| 44-18 | H | 8 | Me | 6 | (CH$_2$)$_3$ |
| 44-19 | H | 6 | F | 5 | (CH$_2$)$_3$ |
| 44-20 | H | 6 | Cl | 5 | (CH$_2$)$_3$ |
| 44-21 | H | — | H | 7 | (CH$_2$)$_6$ |
| 44-22 | H | 8 | Cl | 7 | (CH$_2$)$_6$ |
| 44-23 | H | 8 | Me | 7 | (CH$_2$)$_6$ |
| 44-24 | H | 5 | Cl | 7 | (CH$_2$)$_6$ |
| 44-25 | H | — | H | 8 | (CH$_2$)$_6$ |
| 44-26 | H | 5 | F | 8 | (CH$_2$)$_6$ |
| 44-27 | H | 6 | Me | 8 | (CH$_2$)$_6$ |
| 44-28 | H | 6 | Cl | 8 | (CH$_2$)$_6$ |
| 44-29 | H | — | H | 5 | (CH$_2$)$_6$ |
| 44-30 | H | 8 | F | 5 | (CH$_2$)$_6$ |
| 44-31 | H | 6 | Cl | 5 | (CH$_2$)$_6$ |
| 44-32 | H | 7 | Me | 5 | (CH$_2$)$_6$ |
| 44-33 | H | — | H | 6 | (CH$_2$)$_6$ |
| 44-34 | H | 8 | Me | 6 | (CH$_2$)$_6$ |
| 44-35 | H | — | H | 8 | (CH$_2$)$_4$ |
| 44-36 | H | 5 | Cl | 8 | (CH$_2$)$_4$ |
| 44-37 | H | 5 | Me | 8 | (CH$_2$)$_4$ |
| 44-38 | H | 7 | Me | 8 | (CH$_2$)$_4$ |
| 44-39 | H | 5 | Cl | 7 | (CH$_2$)$_4$ |
| 44-40 | H | 8 | Cl | 7 | (CH$_2$)$_4$ |
| 44-41 | H | — | H | 7 | (CH$_2$)$_4$ |
| 44-42 | H | — | H | 6 | (CH$_2$)$_4$ |
| 44-43 | H | 8 | Me | 6 | (CH$_2$)$_4$ |
| 44-44 | H | 7 | Cl | 6 | (CH$_2$)$_4$ |
| 44-45 | H | 6 | Cl | 7 | (CH$_2$)$_4$ |
| 44-46 | H | — | H | 5 | (CH$_2$)$_4$ |
| 44-47 | H | 8 | Me | 5 | (CH$_2$)$_4$ |
| 44-48 | H | 6 | Cl | 5 | (CH$_2$)$_4$ |
| 44-49 | H | — | H | 8 | (CH$_2$)$_5$ |
| 44-50 | H | 5 | Cl | 8 | (CH$_2$)$_5$ |
| 44-51 | H | 7 | Cl | 8 | (CH$_2$)$_5$ |
| 44-52 | H | — | H | 7 | (CH$_2$)$_5$ |
| 44-53 | H | 6 | Cl | 7 | (CH$_2$)$_5$ |
| 44-54 | H | 5 | Me | 7 | (CH$_2$)$_5$ |
| 44-55 | H | — | H | 5 | (CH$_2$)$_5$ |
| 44-56 | H | 6 | F | 5 | (CH$_2$)$_5$ |
| 44-57 | H | 7 | Me | 5 | (CH$_2$)$_5$ |
| 44-58 | H | — | H | 6 | (CH$_2$)$_5$ |
| 44-59 | H | 7 | Me | 6 | (CH$_2$)$_5$ |
| 44-60 | H | 8 | Cl | 6 | (CH$_2$)$_5$ |
| 44-61 | H | 8 | Cl | 7 | CH$_2$ |
| 44-62 | H | — | H | 7 | CH$_2$ |
| 44-63 | H | 5 | Cl | 7 | CH$_2$ |
| 44-64 | H | 6 | Cl | 7 | CH$_2$ |
| 44-65 | H | 5 | F | 7 | CH$_2$ |
| 44-66 | H | — | H | 7 | (CH$_2$)$_2$ |
| 44-67 | H | 6 | Cl | 7 | (CH$_2$)$_5$ |
| 44-68 | CH$_3$ | — | H | 7 | CH$_2$ |
| 44-69 | CH$_3$ | — | H | 7 | (CH$_2$)$_2$ |
| 44-70 | CH$_3$ | — | H | 7 | (CH$_2$)$_5$ |
| 44-71 | CH$_3$ | — | H | 7 | (CH$_2$)$_6$ |
| 44-72 | CH$_3$ | — | H | 8 | (CH$_2$)$_3$ |
| 44-73 | CH$_3$ | — | H | 5 | (CH$_2$)$_3$ |
| 44-74 | CH$_3$ | — | H | 6 | (CH$_2$)$_3$ |
| 44-75 | (CH$_3$)$_2$CH | — | H | 7 | (CH$_2$)$_3$ |
| 44-76 | C$_6$H$_5$CH$_2$ | — | H | 7 | (CH$_2$)$_3$ |
| 44-77 | H | 8 | OMe | 7 | (CH$_2$)$_3$ |
| 44-78 | H | 5 | OMe | 7 | (CH$_2$)$_3$ |
| 44-79 | H | 6 | OMe | 7 | (CH$_2$)$_3$ |
| 44-80 | H | 6 | OCH(CH$_3$)$_2$ | 7 | (CH$_2$)$_3$ |

EXAMPLE 45

Methyl 4-[(2,3-Dihydro-2-oxo-6-chloro-1H-imidazo[4,5-b]quinolin-7-y)oxy]butanoate

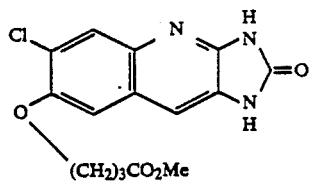

This compound is prepared by dissolving 4-[(2,3-dihydro-2-oxo-6-chloro-2H-imidazo[4,5-b]quinolin-7-yl)oxo]butyric acid in methanol saturated with hydrogen chloride. When esterification is complete (generally from 2 to 12 hours), the mixture is concentrated and the product isolated as the hydrochloride salt or converted to free base by treatment with an alkali base such as sodium hydroxide or potassium carbonate.

In an analogous manner, the remaining acids of Example 44 are converted to the corresponding methyl ester.

EXAMPLE 46

N-Cyclohexyl-N-methyl-4-[(2,3-dihydro-2-oxo-6-chloro-1H-imidazo[4,5-b]quinolin-7-yl)oxy]butanamide

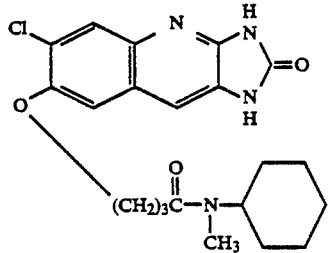

This compound may be prepared from 4-[(2,3-dihydro-2-oxo-6-chloro-1H-imidazo[4,5-b]quinolin-7-yl)oxo]butyric acid and N-methylcyclohexylamine according to the procedure of Example 15.

In an analogous manner, the remaining acids of Example 44 can be converted to the corresponding N-cyclohexylamide with N-methylcyclohexylamine.

EXAMPLE 47

1,3-Dihydro-7-[3-(phenylsulfonyl)propoxy]-2H-imidazo[4,5-b]quinolin-2-one

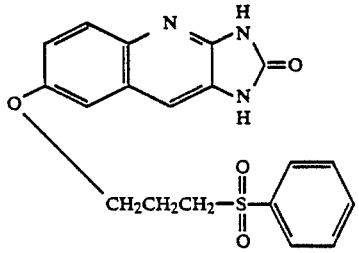

This compound, m.p. 284°-287° C. (dec.), was prepared analogous to Example 35 from 5-[[2-nitro-5-[3-(phenylsulfonyl)propoxy]phenyl]methylene]-2,4-imidazolidinedione.

Anal. Calcd. for $C_{19}H_{17}N_3O_4S$: C, 59.52; H, 4.47; N, 10.96. Found: C, 59.28; H, 4.57; N, 11.18.

1,3-Dihydro-7-[3-[(4-chlorophenyl)sulfonyl]propoxy]-2H-imidazo[4,5-b]quinolin-2-one was analogously prepared from 5-[[2-nitro-5-[3-[(4-chlorophenyl)sulfonyl]propoxy]phenyl]methylene]-2,4-imidazolidinedione.

EXAMPLE 48

1,3-Dihydro-1-methyl-7-[3-(phenylsulfonyl)propoxy]-2H-imidazo[4,5-b]quinolin-2-one

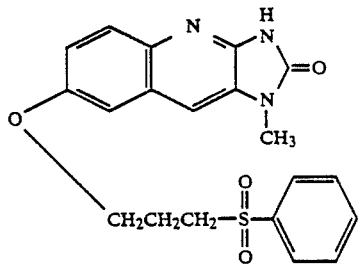

This compound, m.p. 245°-247° C. (dec.), was prepared analogous to Example 35 from 1-methyl-5-[[2-nitro-5-[3-(phenylsulfonyl)propoxy]phenyl]methylene]-2,4-imidazolidinedione.

Anal. Calcd. for $C_{20}H_{19}N_3O_4S$: C, 60.44; H, 4.82; N, 10.57. Found: C, 60.12; H, 4.94; N, 10.95.

EXAMPLE 49

4-[(2,3-Dihydro-2-oxo-1H-imidazo[4,5-b]quinolin-7-yl)oxy]-N-(1-ethylpropyl)butanamide

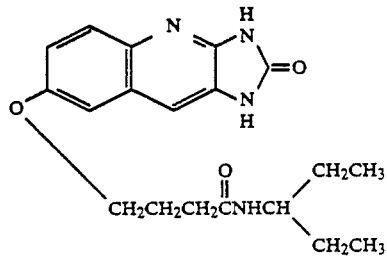

This compound, m.p. 312°-314° C., was prepared from 4-[(2,3-dihydro-2-oxo-1H-imidazo[4,5-b]quinolin-7-yl)oxy]butyric acid and 1-ethylpropylamine.

Anal. Calcd. for $C_{19}H_{24}N_4O_3$: C, 64.03; H, 6.79; N, 15.72. Found: C, 64.12; H, 6.70; N, 15.87.

EXAMPLE 50

N-[4-[(2,3-Dihydro-2-oxo-1H-imidazo[4,5-b]quinolin-7-yl)oxy]-1-oxobutyl]glycine ethyl ester

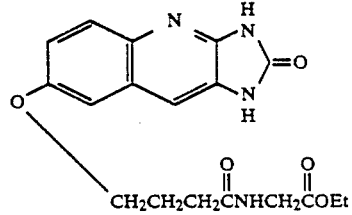

This compound, m.p. 274°–276° C., was prepared analogously to Example 15 from 4-[(2,3-dihydro-2-oxo-1H-imidazo[4,5-b]quinolin-7-yl)oxy]butyric acid and glycine ethyl ester.

Anal. Calcd. for $C_{18}H_{20}N_4O_5$: C, 58.06; H, 5.41; N, 15.05. Found: C, 58.00; H, 5.38; N, 15.26.

EXAMPLE 51

2-[(2,3-Dihydro-2-oxo-1H-imidazo[4,5-b]quinolin-7-yl)oxy]ethyl Acetate

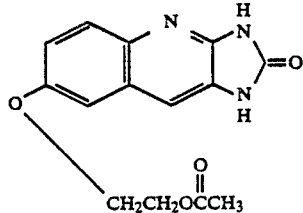

This compound, m.p. 299°–302° C. (dec.), was prepared analogous to Example 10 (using acetonitrile in place of methanol for the iodine treatment) from 2-[3-[(2,4-dioxoimidazolidin-5-ylidene)methyl]-4-nitrophenoxy]ethyl acetate.

Anal. Calcd. for $C_{14}H_{13}N_3O_4$: C, 58.53; H, 4.56; N, 14.63. Found: C, 58.19; H, 4.44; N, 14.95.

EXAMPLE 52

3-[(2,3-Dihydro-1H-imidazo[4,5-b]quinolin-7-yl)oxy]propyl Acetate

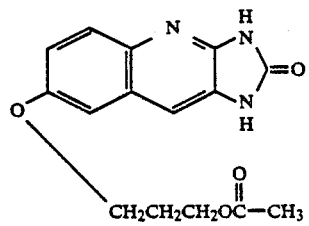

This compound, m.p. 301°–303° C., was prepared analogous to Example 10 (using acetonitrile in place of methanol for the iodine treatment) from 3-[3-[(2,4-dioxoimidazolidin-5-ylidene)methyl]-4-nitrophenoxy]propyl acetate.

Anal. Calcd. for $C_{15}H_{15}N_3O_4$: C, 59.80; H, 5.02; N, 13.95. Found: C, 59.83; H. 5.09; N, 14.12.

What is claimed is:

1. A compound of the formula

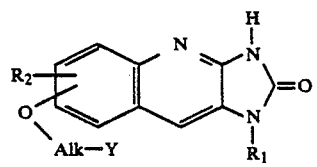

wherein $R_1$ is hydrogen, lower alkyl, benzyl;

$R_2$ is hydrogen, halogen, lower alkyl, lower alkoxy;

Alk is an unbranched or branched alkylene chain of 1 to 8 carbon;

Y is hydroxyl and esters thereof formed with an alkanoic acid of 1 to 6 carbon atoms or phenylalkanoic acid of 7-12 carbon atoms, alkoxy wherein with Alk the number of carbon atoms ranges from 2 to 10, oxo forming a ketone with Alk, di-(lower alkyl)amino, $-CO_2H$, $-CO_2R_3$ wherein $R_3$ is lower alkyl;

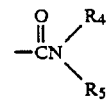

wherein $R_4$ is hydrogen, lower a alkyl, benzyl, cyclohexyl, $-(CH_2)_nCO_2R_6$ wherein n is the integer 1 to 8 and the alkylene chain $(CH_2)_n$ is unbranched or branched and $R_6$ is hydrogen or lower alkyl; $R_5$ is hydrogen, lower alkyl, benzyl, adamentanamyl, cycloalkyl of 3 to 7 carbon atoms wherein the cycloalkyl ring is unsubstituted or substituted with lower alkyl or lower alkoxy;

$R_4$ and $R_5$ are joined together to form 1-morpholinyl, piperidinyl optionally substituted with $-CO_2R_7$ is hydrogen or lower alkyl, 1-(4-phenylpiperazinyl) wherein phenyl is unsubstituted or independently substituted with up to 2 halogen, lower alkyl, or lower alkoxy groups;

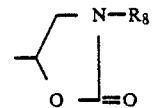

wherein $R_8$ is lower alkyl;

wherein $R_8$ is lower alkyl;

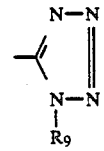

wherein $R_9$ is lower alkyl, cycloalkyl of 5 to 7 carbon atoms; $-SO_2$—phenyl wherein phenyl is unsubstituted or independently substituted with up to 2 halogen, lower alkyl or lower alkoxy;

or a pharmaceutically acceptable salt thereof.

2. The compound of claim 1 wherein Y is $CO_2H$.

3. The compound of claim 1 wherein Y is $CO_2H$, and $R_1$ and $R_2$ are hydrogen.

4. The compound of claim 1 wherein Y is $CO_2R_5$.

5. The compound of claim 1 wherein Y is $CO_2R_3$, and $R_1$ and $R_2$ are hydrogen.

6. The compound of claim 1 or a pharmaceutically acceptable salt thereof which is 4-[(2,3-dihydro-2-oxo-1H-imidazo[4,5-b]quinolin-7-yl)oxy]butanoic acid.

7. The compound of claim 1 or a pharmaceutically acceptable salt thereof which is 4-[(2,3-dihydro-1-methyl-2-oxo-1H-imidazo[4,5-b]quinolin-7-yl)oxy]butanoic acid.

8. The compound of claim 1 or a pharmaceutically acceptable salt thereof which is 2-[(1,3-dihydro-2-oxo-2H-imidazo[4,5-b]quinolin-7-yl)oxy]acetic acid.

9. The compound of claim 1 or a pharmaceutically acceptable salt thereof which is 5-[(2,3-dihydro-2-oxo-1H-imidazo[4,5-b]quinolin-7-yl)oxy]pentanoic acid.

10. The compound of claim 1 or a pharmaceutically acceptable salt thereof which is 5-[(2,3-dihydro-1-methyl-2-oxo-1H-imidazo[4,5-b]quinolin-7-yl)oxy]pentanoic acid.

11. The compound of claim 1 or a pharmaceutically acceptable salt thereof which is methyl 4-[(2,3-dihydro-2-oxo-1H-imidazo[4,5-b]quinolin-7-yl)oxy]butanoate.

12. The compound of claim 1 or a pharmaceutically acceptable salt thereof which is methyl 4-[(2,3-dihydro-1-methyl-2-oxo-1H-imidazo[4,5-b]quinolin-7-yl)oxy]butanoate.

13. The compound of claim 1 or a pharmaceutically acceptable salt thereof which is ethyl[(2,3-dihydro-2-oxo-1H-imidazo[4,5-b]quinolin-7-yl)oxy]acetate.

14. The compound of claim 1 or a pharmaceutically acceptable salt thereof which is methyl 5-[(2,3-dihydro-2-oxo-1H-imidazo[4,5-b]quinolin-7-yl)oxy]pentanoate.

15. The compound of claim 1 or a pharmaceutically acceptable salt thereof which is methyl 5-[(2,3-dihydro-1-methyl-2-oxo-1H-imidazo[4,5-b]quinolin-7-yl)oxy]pentanoate.

16. The compound of claim 1 or a pharmaceutically acceptable salt thereof which is 4-[4-[(2,3-dihydro-2-oxo-1H-imidazo-[4,5-b]quinolin-7-oxy]-1-oxobutyl]morpholine.

17. The compound of claim 1 or a pharmaceutically acceptable salt thereof which is 4-[(2,3-dihydro-2-oxo-1H-imidazo[4,5-b]quinolin-7-yl)oxy]-N-(tricyclo[3.3.1³,⁷]decan-7-yl)butanamide.

18. The compound of claim 1 or a pharmaceutically acceptable salt thereof which is N-cyclopentyl-4-[(2,3-dihydro-2-oxo-1H-imidazo[4,5-b]quinolin-7-yl)oxy]butanamide.

19. The compound of claim 1 or a pharmaceutically acceptable salt thereof which is N-cyclohexyl-4-[(2,3-dihydro-2-oxo-1H-imidazo[4,5-b]quinolin-7-yl)oxy]butanamide.

20. The compound of claim 1 or a pharmaceutically acceptable salt thereof which is N-cyclohexyl-4-[(2,3-dihydro-1-methyl-2-oxo-1H-imidazo[4,5-b]quinolin-7-yl)oxy]butanamide.

21. The compound of claim 1 or a pharmaceutically acceptable salt thereof which is N-cycloheptyl-4-[(2,3-dihydro-2-oxo-1H-imidazo[4,5-b]quinolin-7-yl)oxy]butanamide.

22. The compound of claim 1 or a pharmaceutically acceptable salt thereof which is N-cyclohexyl-N-[4-[(2,3-dihydro-2-oxo-1H-imidazo-[4,5-b]quinolin-7-yl)oxy]-1-oxobutyl]glycine methyl ester.

23. The compound of claim 1 or a pharmaceutically acceptable salt thereof which is N-cycloheptyl-N-methyl-4-[(2,3-dihydro-2-oxo-1H-imidazo[4,5-b]quinolin-7-yl)oxy]butanamide.

24. The compound of claim 1 or a pharmaceutically acceptable salt thereof which is N-cycloheptyl-4-[(2,3-dihydro-1-methyl-2-oxo-1H-imidazo[4,5-b]quinolin-7-yl)oxy]-N-methylbutanamide.

25. The compound of claim 1 or a pharmaceutically acceptable salt thereof which is 1-[4-[(2,3-dihydro-2-oxo-1H-imidazo[4,5-b]quinolin-7-yl)oxy]-1-oxobutyl]piperidine.

26. The compound of claim 1 or a pharmaceutically acceptable salt thereof which is 1-[4-[(2,3-dihydro-1-methyl-2-oxo-1H-imidazo[4,5-b]quinolin-7-yl)oxy]-1-oxobutyl]piperidine.

27. The compound of claim 1 or a pharmaceutically acceptable salt thereof which is 1-[4-[(2,3-dihydro-2-oxo-1H-imidazo[4,5-b]-quinolin-7-yl)oxy]-1-oxobutyl]-4-phenylpiperazine.

28. The compound of claim 1 or a pharmaceutically acceptable salt thereof which is N-cyclohexyl-5-[(2,3-dihydro-1-methyl-2-oxo-1H-imidazo[4,5-b]quinolin-7-yl)oxy]-N-methylpentanamide.

29. The compound of claim 1 or a pharmaceutically acceptable salt thereof which is N-cycloheptyl-5-[(2,3-dihydro-1-methyl-2-oxo-1H-imidazo[4,5-b]quinolin-7-yl)oxy]-N-methylpentanamide.

30. The compound of claim 1 or a pharmaceutically acceptable salt thereof which is ethyl 1-[4-[(2,3-dihydro-2-oxo-1H-imidazo[4,5-b]quinolin-7-yl)oxy]-1-oxobutyl]-4-piperidinecarboxylate.

31. The compound of claim 1 or a pharmaceutically acceptable salt thereof which is N-cyclohexyl-N-methyl-4-[(2,3-dihydro-2-oxo-1H-imidazo[4,5-b]quinolin-7-yl)oxy]butanamide.

32. The compound of claim 1 or a pharmaceutically acceptable salt thereof which is N-cyclohexyl-N-methyl-4-[(2,3-dihydro-1-methyl-2-oxo-1H-imidazo[4,5-b]quinolin-7-yl]oxo]butanamide.

33. The compound of claim 1 or a pharmaceutically acceptable salt thereof which is N-cyclohexyl-N-methyl-5-[(2,3-dihydro-2-oxo-1H-imidazo[4,5-b]quinolin-7-yl)oxo]pentanamide.

34. The compound of claim 1 or a pharmaceutically acceptable salt thereof which is N-cycloheptyl-N-methyl-5-[(2,3-dihydro-2-oxo-1H-imidazo[4,5-b]quinolin-7-yl)oxy]pentanamide.

35. The compound of claim 1 or a pharmaceutically acceptable salt thereof which is 7-[(2-diethylamino)ethoxy]-1,3-dihydro-2H-imidazo[4,5-b]quinolin-2-one.

36. The compound of claim 1 or a pharmaceutically acceptable salt thereof which is 7-[4-(phenylsulfonyl)butoxy]-1,3-dihydro-2H-imidazo[4,5-b]quinolin-2-one.

37. The compound of claim 1 or a pharmaceutically acceptable salt thereof which is 7-[4-(1-cyclohexyl-1H-tetrazol-5-yl)butoxy]-1,3-dihydro-2H-imidazo[4,5-b]-quinolin-2-one.

38. The compound of claim 1 or a pharmaceutically acceptable salt thereof which is 7-(2-ethoxyethoxy)-1,3-dihydro-2H-imidazo[4,5-b]quinolin-2-one.

39. The compound of claim 1 or a pharmaceutically acceptable salt thereof which is 1,3-dihydro-7-(3-hydroxypropoxy)-2H-imidazo[4,5-b]quinolin-2-one.

40. The compound of claim 1 or a pharmaceutically acceptable salt thereof which is 1,3-dihydro-7-(4-oxopentoxy)-2H-imidazo[4,5-b]quinolin-2-one.

41. The compound of claim 1 or a pharmaceutically acceptable salt thereof which is 1,3-dihydro-7-(4-hydroxypentoxy)-2H-imidazo[4,5-b]quinolin-2-one.

42. The compound of claim 1 or a pharmaceutically acceptable salt thereof which is 1,3-dihydro-7-[[3-(1-methylethyl)-2-oxo-5-oxazolidinyl]methoxy]-2H-imidazo[4,5-b]quinolin-2-one.

43. The compound of claim 1 or a pharmaceutically acceptable salt thereof which is 7-[[3-(1,1-dimethylethyl)-2-oxooxazolidin-5-yl]methoxy]-1H-imidazo[4,5-b]quinolin-2(3H)-one.

44. The compound of claim 1 or a pharmaceutically acceptable salt thereof which is 1,3-dihydro-7-[2-hydroxy-3-[(1-methylethyl)-amino]propoxy]-2H-imidazo[4,5-b]quinolin-2-one.

45. The compound of claim 1 or a pharmaceutically acceptable salt thereof which is 1,3-dihydro-7-[3-

(phenylsulfonyl)propoxy]-2H-imidazo[4,5-b]quinolin-2-one.

46. The compound of claim 1 or a pharmaceutically acceptable salt thereof which is 1,3-dihydro-1-methyl-7-[3-(phenylsulfonyl)-propoxy]-2H-imidazo[4,5-b]quinolin-2-one.

47. The compound of claim 1 or a pharmaceutically acceptable salt thereof which is 4-[(2,3-dihydro-2-oxo-1H-imidazo[4,5-b]quinolin-7-yl)oxy]-N-(1-ethylpropyl)-butanamide.

48. The compound of claim 1 or a pharmaceutically acceptable salt thereof which is N-[4-[(2,3-dihydro-2-oxo-1H-imidazo[4,5-b]-quinolin-7-yl)oxy]-1-oxobutyl]glycine ethyl ester.

49. The compound of claim 1 or a pharmaceutically acceptable salt thereof which is 2-[(2,3-dihydro-2-oxo-1H-imidazo[4,5-b]quinolin-7-yl)oxy]ethyl acetate.

50. The compound of claim 1 or a pharmaceutically acceptable salt thereof which is 3-[(2,3-dihydro-1H-imidazo[4,5-b]quinolin-7-yl)oxy]propyl acetate.

51. A method for inhibiting cyclic AMP phosphodiesterase in a mammal which comprises administering a therapeutically effective amount of a compound of claim 1 or a pharmaceutically acceptable salt thereof.

52. A method for increasing heart inotropic activity which comprises administering to a warm blooded animal, in need of such treatment a therapeutically effective amount of a compound of claim 1 or a pharmaceutically acceptable salt thereof.

53. The pharmaceutical composition for inhibiting cyclic AMP phosphodiesterase comprising a therapeutically effective amount of a compound of claim 1 or a pharmaceutically acceptable acid addition salt thereof and a pharmaceutical carrier.

54. A method for inhibiting blood platelet aggregation in a mammal which comprises administering a therapeutically effective amount of a compound of claim 1 or a pharmaceutically acceptable salt thereof.

55. The pharmaceutical composition for inhibiting blood platelet aggregation comprising a therapeutically effective amount of a compound of claim 1 or a pharmaceutically acceptable acid addition salt thereof and a pharmaceutical carrier.

56. The pharmaceutical composition for increasing heart inotropic activity comprising a therapeutically effective amount of a compound of claim 1 or a pharmaceutically acceptable acid addition salt thereof and a pharmaceutical carrier.

* * * * *